United States Patent
Shankey et al.

(10) Patent No.: US 10,073,082 B2
(45) Date of Patent: Sep. 11, 2018

(54) PROTEASOME INHIBITION ASSAY AND METHODS OF USE

(71) Applicants: UNIVERSITY HEALTH NETWORK, Toronto (CA); BECKMAN COULTER, INC., Brea, CA (US)

(72) Inventors: T. Vincent Shankey, Miami, FL (US); Sergei Gulnik, Miami, FL (US); Lidice L. Lopez, Miami, FL (US); David W. Hedley, Toronto (CA); Sue Chow, Markham (CA)

(73) Assignees: Beckman Coulter, Inc., Brea, CA (US); University Health Network, Toronto (CA)

( * ) Notice: Subject to any disclaimer, the term of this patent is extended or adjusted under 35 U.S.C. 154(b) by 0 days.

(21) Appl. No.: 15/028,846

(22) PCT Filed: Oct. 3, 2014

(86) PCT No.: PCT/US2014/058948
§ 371 (c)(1),
(2) Date: Apr. 12, 2016

(87) PCT Pub. No.: WO2015/057402
PCT Pub. Date: Apr. 23, 2015

(65) Prior Publication Data
US 2016/0258934 A1 Sep. 8, 2016

Related U.S. Application Data

(60) Provisional application No. 61/892,778, filed on Oct. 18, 2013.

(51) Int. Cl.
| | | |
|---|---|---|
| *G01N 33/49* | (2006.01) |
| *G01N 33/53* | (2006.01) |
| *G01N 33/50* | (2006.01) |
| *C12Q 1/37* | (2006.01) |
| *G01N 33/58* | (2006.01) |
| *G01N 15/14* | (2006.01) |
| *C07K 14/47* | (2006.01) |
| *C07K 16/18* | (2006.01) |
| *G01N 15/00* | (2006.01) |
| *G01N 15/10* | (2006.01) |

(52) U.S. Cl.
CPC ......... *G01N 33/5041* (2013.01); *C12Q 1/37* (2013.01); *G01N 15/14* (2013.01); *G01N 33/4915* (2013.01); *G01N 33/5011* (2013.01); *G01N 33/5047* (2013.01); *G01N 33/53* (2013.01); *G01N 33/582* (2013.01); *C07K 14/47* (2013.01); *C07K 16/18* (2013.01); *G01N 2015/008* (2013.01); *G01N 2015/1006* (2013.01); *G01N 2015/149* (2013.01); *G01N 2333/4704* (2013.01); *G01N 2440/14* (2013.01)

(58) Field of Classification Search
None
See application file for complete search history.

(56) References Cited

U.S. PATENT DOCUMENTS

2007/0048812 A1    3/2007    Moravec et al.

OTHER PUBLICATIONS

Kingeter et al (2010. Journal of Immunology. 185, pp. 1-5 as printed).*
Karin et al 1999 (Oncogene. 18: 6867-6874).*
Hu et al 2003 (Cytokine. 21: 286-294).*
International Search Report and Written Opinion for International Application No. PCT/US2014/058948 dated Jan. 27, 2015 (13 pages).
Marfella et al. "Increased Activity of the Ubiquitin-Proteasome System in Patients with Symptomatic Carotid Disease Is Associated with Enhanced Inflammation and May Destabilize the Atherosclerosis Plaque." J. of the Am. College of Cardiology. vol. 47, No. 12. Jun. 20, 2006. pp. 2444-2455.
Place et al. "HDAC inhibition prevents NF-kappaB acivication by suppressing proteasome activity: Down-regulation of proteasome subunit expression stablizes IkappaBalpha." Biochem. Pharm. vol. 70, No. 3. Aug. 1, 2005, pp. 394-406.
Ponnappan et al. "Studies into the effect of tyrosine phosphatase inhibitor phenylarsine oxide on nfkappab activation in T lymphocytes during aging: evidence for altered IkappaB-alpha phosphorylation and degradation." Exp. Gerontology. vol. 34. No. 1. Jan. 1, 1999, pp. 95-107.

* cited by examiner

*Primary Examiner* — Zachary C Howard
(74) *Attorney, Agent, or Firm* — Merchant & Gould, P.C.

(57) ABSTRACT

Assays that can measure the effect of proteasome inhibitors on target cells in a biological sample are provided. The assays include evaluation of the effects of proteasome inhibitors on proteasome activity in cells in a biological sample.

22 Claims, 21 Drawing Sheets

PROTEASOME INHIBITION ASSAY AND METHODS OF USE

CROSS-REFERENCE TO RELATED APPLICATION(S)

This application is being filed on Oct. 3, 2014, as a PCT International Patent application and claims priority to U.S. Patent Application Ser. No. 61/892,778 filed on Oct. 18, 2013, the disclosure of which is incorporated herein by reference in its entirety.

BACKGROUND OF THE INVENTION

The proteasome is a protein complex that is present in all eukaryotic cells, and degrades intracellular proteins that are specifically marked for removal. As such, it regulates cell proliferation, apoptosis, and cell differentiation. In addition, it removes proteins that are misfolded, changed by aging, or damaged by oxidation. Empirical evidence suggests that cancer cells rely more heavily on intact proteasomal function, in part because they divide more frequently and in part because many of their regulatory pathways are disrupted due to aberrant protein structure.

Inhibition of proteasome activity is therefore a therapeutic strategy for treating cancer. For example, the proteasome inhibitor Bortezomib (VELCADE®) has been approved by the FDA and is being used as a first-line therapeutic to treat multiple myeloma and mantle cell lymphoma. Carfilzomib (KYPROLIS®) was approved by the FDA for the treatment of patients with multiple myeloma who demonstrate disease progression after receiving two prior therapies, including Bortezomib and an immunomodulatory agent. Bortezomib as well as new proteasome inhibitors are now in clinical trials to treat different cancers, including hematological and solid tumors.

Current proteasome inhibitors can exhibit significant toxicity, which varies significantly from patient to patient. At present, there is no biomarker assay to monitor the differential impact of proteasome inhibitors on normal vs tumor cell populations, making it difficult to establish a proper therapeutic window, or optimize drug levels in individual patients.

A variety of assays have been used in clinical research to assess either proteasome activity, or measure proteasome activity in blood. The functioning proteasome is a proteolytic complex with chymotrypsin-like, trypsin-like, and peptidyl-glutamyl caspase-like protease activity. Current biochemical assays used to measure proteasome activity utilize quenched fluorogenic peptide substrates that are non-fluorescent until the peptide is cleaved, releasing a highly fluorescent peptide fragment that can be measured using a fluorimeter. The rate of fluorogen appearance can be used to determine the concentration of proteasomal enzymes and their activity. In the presence of a proteasome inhibiting compound (e.g. Bortezomib), generation of fluorescence is inhibited and the rate of fluorescence appearance can be used to measure the effect of inhibitor on proteasome activity.

These assays require a cell lysate because fluorogenic substrates penetrate intact cells poorly, and fluorescent product can easily diffuse out of the cell. It is therefore difficult to differentiate between a small number of target cells containing high concentrations of proteasomes (e.g., cancer cells) and a large number of normal cells containing low concentrations proteasomes. In addition, unless the target cells can first be purified, it is not possible to distinguish the impact of any inhibitor on the target cells as opposed to normal cell populations in a sample. Thus, in order to determine the effectiveness of a proteasome inhibitor in a given patient, the proteasome activity of the total white blood cell extracts from that patient are compared before and after drug administration. As a result, these cell free assays provide little to no information on the functional effectiveness of inhibitors inside a target cell population. In addition, the dilution introduced by cell lysis may cause dissociation of proteasome inhibitors with faster off-rates, making accurate measurement problematic.

There is a need for an assay capable of distinguishing target cells in a cell population and measuring proteasome activity and inhibition thereof by proteasome-specific inhibitors in selected target cells within the cell population. There is also a need for a proteasome activity assay that can be used in whole blood, without requiring cell lysis, thus preventing sample dilution.

BRIEF SUMMARY OF THE INVENTION

An assay for detecting and monitoring proteasome activity in target cells, such as hematopoietic cells or neoplastic cells, is disclosed. The assays of the disclosure generally include: activating one or more target cells in a biological sample with an IκB degradation agonist; terminating the action of the IκB degradation agonist by contacting the biological sample with a fixation and/or permeabilization reagent, contacting the activated sample with a labeled binding agent capable of binding IκB; detecting the target cells in the activated sample; and determining the amount of labeled binding agent associated with the target cells, thereby detecting proteasome activity in the target cells A particle analyzer, such as a flow cytometer, is generally used to detect the target cells and determine the amount of labeled binding agent associated with the target cells The amount of labeled binding agent associated with the target cells is indicative of the amount of IκB in the cells.

The assays can also include treating the biological sample containing target cells of interest with or without a proteasome effector prior to contacting the sample with the IκB degradation agonist. The effect of the proteasome effector on proteasome activity can be determined by comparing the IκB level in target cells treated with the proteasome effector to the IκB level in control cells activated with the IκB degradation agonist but not treated with the proteasome effector. A decrease in IκB degradation compared to the control is indicative of inhibition of proteasome activity.

The assays can further include a second labeled binding agent. The biological sample can be contacted with the second labeled binding agent before, simultaneous, or subsequent to the contacting the biological sample with the first labeled binding agent. In embodiments, the second labeled binding agent specifically binds a subtype of hematopoietic cell or neoplastic cell. If the binding target for the second labeled binding agent is extracellular, the biological sample can be contacted with the second labeled binding agent before the cells are fixed and/or permeabilized.

The assays can further include a third labeled binding agent. Typically, the third labeled binding agent is directed to intracellular binding targets, such as activatable signaling proteins including but not limited to ERK, Akt, p38, SAPK, or S6 in phosphorylated form. The biological sample is typically contacted with the fixative agent before contacting the biological sample with the third labeled binding agent(s). The fixed biological sample is generally contacted with the third labeled binding agent(s) concurrently or subsequent to permeabilization of the fixed biological sample with the permeabilizing agent.

The disclosed assays can be used to screen candidate compounds, drugs or biomolecules for proteasome inhibitory activity to identity proteasome inhibitors for treating a disease or disorder, such as cancer. The disclosed assays are also useful for monitoring the treatment of a disease or disorder in a patient, such as cancer. The assays can be used to evaluate the effects of therapy comprising a proteasome effector, such as a proteasome inhibitor, on proteasome activity and other cellular processes in target cells (e.g., cancer cells) and non-target cells (e.g., non-cancer cells) in a biological sample from the patient and allows the clinician to monitor treatment and adjust to therapeutic regimen based on the effects in an individual patient. The assays of the disclosure are also useful for detecting modulation of proteasome activity in a patient by determining proteasome activity in a biological sample obtained from the patient before and after treatment with the proteasome effector.

The assays can be provided as a kit in a packaged combination form comprising one of more reagents for use in the assay and instructions for performing the assay methods of the disclosure. The kit generally includes an IκB degradation agonist; a binding agent that specifically binds an IκB protein (e.g., phosphorylated, unphosphorylated, or both); and instructions on how to perform the assay method using these reagents. The binding agent may be labeled or unlabeled. The kit may optionally include reagents for conjugating a label to the binding agents.

The kit can further include one of more binding agents that specifically bind an activatable protein, such as ERK, Akt, S6, p38, and SAPK, or activated (e.g., phosphorylated) form thereof and/or one or more binding agents that specifically bind a cellular surface antigen. The kit can further include a fixative agent, a permeabilizing agent, a denaturing agent for unmasking epitopes, one of more incubation buffers, one or more staining buffers, and/or one or more labeling agents for labeling one of more of the binding agents. The kit can also include one or more control cell populations and/or one or more proteasome effectors for use as a positive or negative control for aid in determining and/or monitoring proteasome activity.

DETAILED DESCRIPTION

The proteasome is involved in regulation or cell proliferation, apoptosis, and cell differentiation in normal cells. The proteasome also removes abnormal proteins that are misfolded, changed through aging, or damaged by oxidation. Cancer cells have been found to rely more heavily on proteasome activity than normal cells, in part because the cancer cells divided more rapidly and in part because many of the normal regulatory pathways are disrupted in the cancer cells. Therefore, the inhibition of proteasome activity has become an important therapeutic target for treating cancers, in particular leukemias and myelomas. However, current methods for monitoring the differential impact of proteasome inhibitors on cellular functions in vivo are deficient and rely on cellular lysates which make it difficult to distinguish the effects of the inhibitor on cancer cells from normal cells.

Biomarker assays that can measure proteasome activity and the effect of proteasome effectors on a variety of cells and in a variety of biological samples are disclosed. The assays do not require cell lysis and thus provide a means to differentiate between target cells (e.g., disease related cells such as cancer cells) and non-target cells in a sample. The assay can also measure proteasome activity and proteasome inhibition in different populations of normal cells. In addition, the assays are also useful to evaluate the effects of proteasome effectors or candidate proteasome effectors on the activation state of particular signal transduction pathway proteins in target cells. Detection of the activation state of these proteins enhances the sensitivity and specificity of the assays of the disclosure.

In normal cells, activation of the NF-κB pathway through a number of different cell surface receptors, including toll-like receptor 4 (TLR4), results in the phosphorylation of the IκBα protein by its upstream kinase IKK. Phosphorylation of IκBα results in its ubiquination, followed by rapid proteasomal degradation. Released NF-κB complexes can then translocate to the nucleus, where they initiate transcriptional activation.

Figure 1:
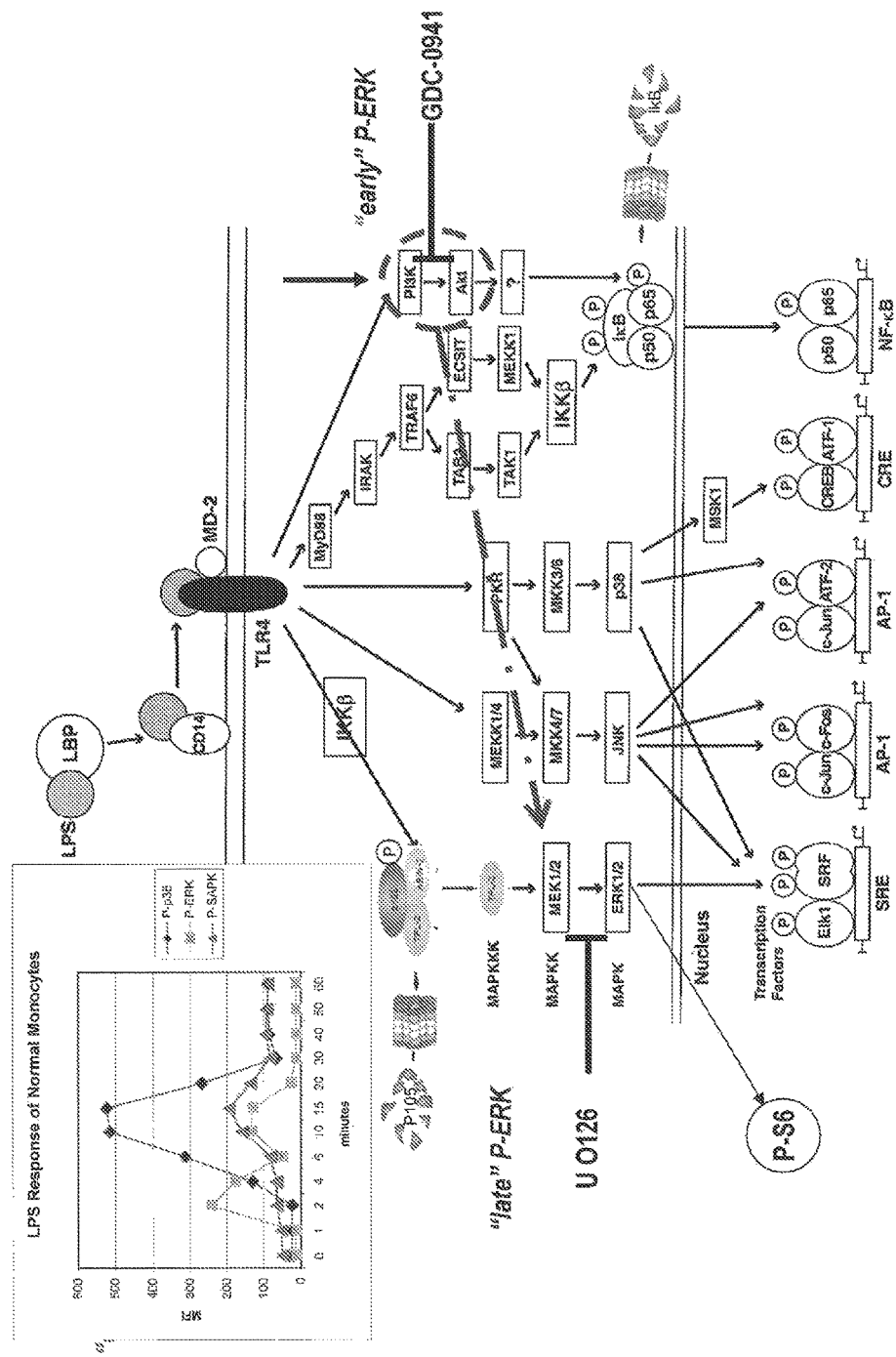
FIG. 1 illustrates LPS-mediated activation of various signal transduction pathways in monocytes. The inset data plot shows the kinetics of activation of three MAP kinases, ERK (squares), p38 (diamonds), and SAPK (triangles) in normal peripheral blood monocytes activated with LPS.

As shown in FIG. 1, exposure of monocytes to a signal transduction activator, such as lipopolysaccharide (LPS), results in phosphorylation of IκB via the TLR4 receptor. IκB normally sequesters the NF-κB complex in the cytoplasm. Phosphorylation of IκB results in its ubiquination, tagging it for destruction by the proteasome. TLR4 activation is unique in that is results in the activation of a number of different, major signaling pathways, including all three MAP kinases, ERK, p38, and SAP/JNK, and the PI3 kinase pathway. As shown in FIG. 1, NFκB, when free of IκB, translocates to the nucleus where it binds to promoter sites, activating specific genes. We have monitored the degradation of IκB in hematopoietic cells with the phosphorylation (e.g., activation) of signaling pathways activated by an IκB degradation agonist, including all three MAP kinases (ERK, p38, and SAPK), Akt (activated by PI3 kinase), and the ribosomal S6 protein (a marker of protein synthesis) and discovered that IκB is a convenient biomarker for measuring and/or monitoring proteasome activity in cells.

The assays of the disclosure generally include: activating one or more target cells in a biological sample with an IκB degradation agonist; contacting the activated sample with a labeled binding agent capable of binding IκB; detecting the target cells in the activated sample; and determining the amount of labeled binding agent associated with the target cells, thereby detecting proteasome activity in the target cells The amount of labeled binding agent associated with the target cells is indicative of the amount of IκB in the cells. The assays can also include treating the biological sample containing target cells of interest with or without a proteasome effector prior to contacting the sample with the IκB degradation agonist. The effect of the proteasome effector on proteasome activity can be determined by comparing the IκB level in target cells treated with the proteasome effector to the IκB level in control cells activated with the IκB degradation agonist but not treated with the proteasome effector. A decrease in IκB degradation compared to the control is indicative of inhibition of proteasome activity.

I. Definitions

Whenever appropriate, terms used in the singular also will include the plural and vice versa. The use of "a" herein means "one or more" unless stated otherwise or where the use of "one or more" is clearly inappropriate. The use of "or" means "and/or" unless stated otherwise. The use of "comprise," "comprises," "comprising," "include," "includes," and "including" are interchangeable and not intended to be limiting. The term "such as" also is not intended to be limiting. For example, the term "including" shall mean "including, but not limited to."

A "proteasome effector" is molecule capable of modifying or modulating the function of a proteasome. As used herein, a proteasome effector can be a chemical substance, compound, drug, biomolecule such as a protein, antibody, or polypeptide, or composition or mixture thereof. In some embodiment, a proteasome effector can also modulate the function of a non-proteasome protein (e.g. a composition capable of modulating another protease, such as HIV protease) as well as a proteasome. In some embodiments, the proteasome effector is a proteasome inhibitor. In some embodiments, the proteasome effector is a proteasome activator.

A "proteasome inhibitor" is a proteasome effector capable of inhibiting proteasome activity. The proteasome inhibitor can be a chemical compound, drug, biomolecule, or composition or mixture thereof. The proteasome inhibitor can be an irreversible covalent proteasome inhibitor (e.g., covalent bond to a proteasome is not significantly hydrolyzed under physiological conditions), a reversible covalent proteasome inhibitor (e.g., covalent bond to a proteasome is significantly hydrolyzed under physiological conditions), or a reversible non-covalent proteasome inhibitor. A proteasome inhibitor is capable of inhibiting a protcosome from proteolyzing (e.g., degrading, cleaving, or destroying) IκB. Thus, in the assays of the disclosure, detecting of IκB levels in a target cell is conveniently used to monitor proteasome activity in the target cell.

The terms "IκB degradation agonist" or "IκB degradation activator" can be used interchangeably and refer to a compound, chemical agent, drug, or biomolecule capable of modulating (e.g., increasing or decreasing the function of) an element of a signal transduction pathway (e.g., activatable protein) wherein the modulation results in the induction of the degradation of IκB in a cell.

"IκB" as used herein refers to the IκB family of proteins which include IκBalpha, IκBbeta, IκBepsilon, IκBgamma, and BCL3. IκB further includes p100 and p105, which are structural motifs common to NF-κB and are considered members of the NF-κB protein family. Degradation of the IκB proteins, including p100 and p105, occurs by ubiquination and proteasomal degradation.

As used herein, a "signal transduction pathway protein" or "activatable protein" refers to a protein that has at least one isoform that corresponds to a specific form of the protein having a particular biological, biochemical, or physical property, e.g., an enzymatic activity, a modification (e.g., post-translational modification, such as phosphorylation), or a conformation. The activatable protein can be activated or inactivated with respect to a particular biological activity, modification, or conformation. "P-" or "-p" can be used to identify a phosphorylated form of an activatable protein, for example P-ERK, P-Akt, P-p38, P-SAPK, or P-S6.

A "binding agent" or "capture molecule" of the invention can be any molecule or complex of molecules capable of specifically binding to a desired target (e.g., protein), such as activated IκB or P-ERK. A binding agent of the invention includes any molecule, e.g., proteins, small organic molecule, antibody or fragment thereof, carbohydrates (including polysaccharides), polynucleotides, lipids, and the like.

The term "antibody" as used herein refers to immunoglobulin molecules and immunologically active portions or fragments of immunoglobulin (Ig) molecules. Such antibodies include, but are not limited to, polyclonal, monoclonal, mono-specific polyclonal antibodies, antibody mimics, chimeric, single chain, Fab, Fab' and F(ab')$_2$ fragments, Fv, and scFv. The antibody may be a monoclonal antibody or a polyclonal antibody.

The binding agent or capture molecule can be labeled with a molecule that can be directly (i.e., a primary label) or indirectly (i.e., a secondary label) detected. The label can be visualized and/or measured or otherwise identified so that its presence or absence can be detected by means of a detectable signal. Examples of suitable labels include, but are not limited to, fluorescent molecules, enzymes (e.g., horseradish peroxidase), particles (e.g., magnetic particles), fluorophores, chromophores, phosphores, chemiluminescers, specific binding molecules (e.g., biotin and streptavidin, digoxin and antidigoxin), and the like.

A "cellular surface antigen" is a molecule that may be contacted by a binding agent that is at least partially exterior to the cell that is associated with the cellular surface antigen.

A "target cell" refers to a cell or population of cells in which proteasome activity is determined and/or monitored. The target cell can be any cell in which it is desirable to determine and/or monitor proteasome activity. Examples of target cells include but are not limited to hematopoietic cells, neoplastic cells, such as cancer cells, and disease associated cells. Examples of cancers include but are not limited to solid tumors, breast cancer, pancreatic cancer, colon cancer, non-small cell lung cancer, leukemias, lymphomas, such as mantle cell lymphoma, and myelomas, such as multiple myeloma. The term "cancer cells" can also be used to refer to cancer or tumor cell lines.

The term "hematopoietic cell" is used herein refers to a cell of any of the blood cell types. Hematopoietic cells include myeloid cells, such as monocytes, macrophages, neutrophils, basophils, eosinophils, erythrocytes, megakaryocytes, platelets, thrombocytes, and dendritic cells, and lymphoid cells, such as T-cells, B-cells, or NK-cells). Hematopoietic cells include hematopoietic stem cells, multipotent progenitor cells, oligopotent progenitor cells, unipotent progenitor cells, lineage-restricted progenitor cells, common myeloid progenitor cells, granulocyte-macrophage progenitor cells, and megakaryocyte-erythroid progenitor cells. A hematopoietic cell may be an erythrocyte, leukocyte, lymphocyte, phagocyte, monocyte, macrophage, granulocyte, basophil, neutrophil, eosinophil, or platelet.

"Contacting", or other verb forms thereof, is used in accordance with its plain ordinary meaning and refers to the process of allowing at least two distinct species (e.g. chemical compounds including biomolecules, or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

II. Exemplary Embodiments

To determine proteasome activity of cells in a biological sample and/or evaluate the effects of a proteasome effector on cells in the biological sample, cells in the sample are activated with an IκB degradation agonist and the degradation of IκB in the cells is detected and/or monitored as described herein to determine and/or monitor proteasome activity. The effects of a proteasome effector on proteasome activity in cells of the biological sample can be detected and/or monitored by activating cells contacted by the proteasome effector with an IκB degradation agonist and detecting and/or monitoring degradation of IκB in the cells as described herein to determine and/or monitor the effects of the proteasome effector on proteasome function in cells of the biological sample.

A. Biological Sample

The biological sample typically includes one or more hematopoietic cells and/or neoplastic cells. Examples of hematopoietic cells include myeloid cells, such as monocytes, macrophages, neutrophils, basophils, eosinophils, erythrocytes, megakaryocytes, platelets, thrombocytes, and dendritic cells, lymphoid cells, such as T-cells, B-cells, and NK-cells, multipotent progenitor cells, oligopotent progenitor cells, unipotent progenitor cells, lineage-restricted progenitor cells, common myeloid progenitor cells, granulocyte-macrophage progenitor cells, and megakaryocyte-erythroid progenitor cells. In some embodiments, the hematopoietic cells are erythrocytes, leukocytes, lymphocytes, phagocytes, monocytes, macrophages, granulocytes, basophils, neutrophils, eosinophils, platelets, or a mixture thereof. In embodiments, the hematopoietic cells comprise peripheral blood monocyte, peripheral blood lymphocyte, or a mixture thereof. The neoplastic cells generally comprise cancer cells. Examples of cancer cells include but are not limited to solid tumors, breast cancer, pancreatic cancer, colon cancer, non-small cell lung cancer, leukemias, lymphomas, such as mantle cell lymphoma, and myelomas, such as multiple myeloma.

The sample can be, for example, blood, bone marrow, spleen cells, lymph, bone marrow aspirates (or any cells obtained from bone marrow), urine (lavage), serum, saliva, cerebral spinal fluid, urine, amniotic fluid, interstitial fluid, feces, mucus, or tissue (e.g., tumor samples, disaggregated tissue, disaggregated solid tumor). In some embodiments, the samples comprise monocytes, lymphocytes, or a mixture thereof. In certain embodiments, the sample is a blood sample. In some embodiments, the blood sample is whole blood. The whole blood can be obtained from the subject using standard clinical procedures. In some embodiments, the sample is a subset of one or more cells of whole blood (e.g., erythrocyte, leukocyte, lymphocyte, phagocyte, monocyte, macrophage, granulocyte, basophil, neutrophil, eosinophil, or platelet).

The sample can be from a human subject, or a commercially significant mammal, including, for example, a monkey, cow, or horse. Samples can also be obtained from household pets, including, for example, a dog or cat. In some embodiments, the subject is a laboratory animal used as an animal model of disease, for example, a mouse, a rat, a rabbit, or guinea pig. The biological sample can be obtained from an individual or subject using standard clinical procedures. The biological sample can also be a sample that was previously obtained from the individual or subject. In some embodiments, a biological sample is obtained from a "naïve" patient who has not undergone treatment with a particular compound or drug, such as a proteasome inhibitor, that may affect proteasome activity. Such a sample may be obtained from "naïve" patient prior to administration of the compound or drug to the patient to treat a disease or disorder, such as cancer. In some embodiments, the naïve patient is an "age-matched" control. The "age-matched" samples are generally obtained from normal individuals of similar age, sex, and race. The age-matched samples can be used as negative controls in the assay methods of the disclosure.

In a typical embodiment, a biological sample is derived from a patient having a disease or disorder that may benefit from treatment with a proteasome effector. Examples of such diseases or disorders include but are not limited to cancer, allergy, and autoimmune disease. Examples of cancer include but are not limited to solid tumors, breast cancer, pancreatic cancer, colon cancer, non-small cell lung cancer, leukemias, lymphomas, such as mantle cell lymphoma, and myelomas, such as multiple myeloma. Evaluation of the effects of therapy comprising a proteasome effector, such as a proteasome inhibitor, on proteasome activity and other cellular processes in target (e.g., cancer, allergy, or autoimmune disease) and non-target cells allows the clinician to monitor treatment and adjust to therapeutic regimen based on the effects in an individual patient. For example, if proteasome activity of non-target (e.g., non-cancer cells, non-disease related cells, non-autoimmune associated cells, or non-allergy related cells) is being adversely affected by the treatment regimen or dosage at an unacceptable level, the regimen or dosage may be adjusted to decrease adverse effects on non-target cells while maintaining a suitable level of proteasome inhibition to kill the target cells.

In some embodiments, the biological samples can be cultured cells, such as cells from normal cell lines or cancer cell lines, or samples derived from laboratory animals, or human subjects not undergoing treatment or before treatment with a proteasome inhibitor to establish a baseline control for proteasome activity. In these embodiments, a proteasome inhibitor can be added to the sample and the effects of the inhibitor on proteasome activity in target cells in the sample can be detected and then compared to proteasome function of the target cells from the disease state.

B. Proteasome Effector

The proteasome effector can be a proteasome inhibitor or proteasome activator or a candidate thereof. Candidate proteasome effectors can be screened according to the assay methods of the disclosure and identified as a proteasome inhibitor or proteasome activator based on the observed effects of the candidate effector on degradation of IκB in a target cell population. In some embodiments, the proteasome effector is a proteasome inhibitor or a candidate proteasome inhibitor. Examples of proteasome inhibitors may be found in Blackburn et al. 2010, Biochem. J., 430: 461-476, which is incorporated herein by reference. In some embodiments, a proteasome inhibitor is a composition capable of modulating the function of a non-proteasome protein (e.g. a composition capable of modulating another protease (e.g. a HIV protease inhibitor)) as well as the proteasome. In some embodiments, a proteasome inhibitor is a boron containing proteasome inhibitor. A proteasome inhibitor may include an aldehyde moiety.

The proteasome inhibitor can be a covalent or non-covalent inhibitor. In an embodiment, the proteasome inhibitor is an irreversible covalent proteasome inhibitor, a reversible covalent proteasome inhibitor, or a reversible non-covalent proteasome inhibitor. Covalent inhibitors are believed to inhibit the chymotrypsin-like activity of the 20S proteasome via the formation of a covalent adduct to the N-terminal threonine on the active site of the beta-subunit. Representative examples of covalent proteasome inhibitors include but are not limited to peptide aldehydes, such as MG-132 and ALLN; peptide vinyl sulfones, such as Ac-YLLN-vs; peptide boronates, such as Bortezomib; peptide epoxyketones, such as epoxomicin and carfilzomib; and beta-lactones, such as lactacystine, salinosporamide. One example of a non-covalent proteasome inhibitor is TMC-95A, which is a natural cyclic peptide and structurally unrelated to the covalent inhibitors discussed above.

Proteasome inhibitors are useful for treating cancer and various inflammatory conditions, including allergy and autoimmune diseases. For example, the proteasome inhibitor Bortezomib (also known as VELCADE® and formerly PS-341) is currently used to treat multiple myeloma and mantle cell lymphoma. Carfilzomib (also known as PR171) has also been approved for the treatment of multiple myeloma under certain conditions. Such compounds are also contemplated for treatment of patients with advanced solid tumors, breast cancer, pancreatic cancer, colon cancer and non-small cell lung cancer. Additional examples of proteasome inhibitors include but are not limited to tripeptide epoxiketone oprozomib, non-peptidic lactone marizomib, and dipeptidyl boronic acid ixazomib.

C. IκB Degradation Agonist

To evaluate the effects of proteasome inhibitors on cells in a biological sample, the cells or biological sample is contacted with an IκB degradation agonist. IκB degradation agonists are capable of modulating (e.g., increasing or decreasing the function of) an element of a signal transduction pathway (e.g., activatable protein) wherein the modulation of the signal transduction pathway results in the induction of the degradation of IκB. In a typical embodiment, the activatable protein is activated through phosphorylation. Examples of activatable proteins include, but are not limited to, IKK complex, ERK, S6, Akt, and p38.

The IκB degradation agonists are typically a compound, chemical agent, drug, or biomolecule. In some embodiments, an IκB degradation agonist increases the degradation of IκB by the proteasome. In some embodiments, a IκB degradation agonist induces the degradation of IκB by the proteasome. In some embodiments, the IκB degradation agonist directly modulates the structure and/or function of the proteasome. In some embodiments, the IκB degradation agonist modulates a non-proteasome molecule that then modulates (directly or indirectly) the proteasome. In some embodiments, the IκB degradation agonist binds an extracellular receptor and activates or inhibits a signal transduction pathway that modulates the function of the proteasome.

Examples of IκB degradation agonists include but are not limited to lipopolysaccharide (LPS), CD40L, PMA, IL-1, IL-4, G-CSF, SCF, Flt-3 ligand, GM-CSF, TGF, anti-CD28, anti-CD3/CD28, and TNF-alpha. The LPS can be naturally occurring or synthetic and encompasses synthetically or semi-synthetically prepared variants. The LPS can be derived from the cell wall of many Gram negative bacteria as well as other natural or synthetic sources. In an embodiment, the IκB degradation agonist is a TLR4 receptor agonist that stimulates activation of one more MAP kinases and/or the PI3 kinase pathway. Examples of suitable TLR4 agonists include but are not limited to LPS, glucuronoxylomannan from *Cryptococcus*, and monophosphoryl lipid A. The IκB degradation agonists can be activators of other receptor tyrosine kinase activators to stimulate monocytes or other target cells, for example TNF-alpha, CD40L, or TGF to activate monocytes or lymphocytes, GM-CSF to activate the JAK/STAT pathway in peripheral blood monocytes, IL-4 to activate the JAK/STAT pathway in peripheral blood lymphocytes, or anti-CD28 and anti-CD3/CD28 to activate T cells.

In an embodiment, one signal transduction pathway activated by the IκB degradation agonists of the disclosure is the mitogen activated protein kinase (MAPK) pathway. The MAPK pathway is a signal transduction pathway that effects gene regulation, and which controls cell proliferation and differentiation in response to extracellular signals. This pathway is shown in FIG. 1 and includes ERK1/2. The MAPK pathway can be activated by IκB degradation agonists such as LPS, cytokines such as IL-1 and TNF, CD40 Ligand, and PMA.

Another signal transduction pathway activated by IκB degradation agonists of the disclosure is the PI3K pathway. This pathway is also shown in FIG. 1. The PI3K pathway is a phosphatidylinositol 3-kinase pathway which mediates and regulates cellular apoptosis. The PI3K pathway also mediates cellular processes, including proliferation, growth, differentiation, motility, neovascularization, mitogenesis, transformation, viability, and senescence. The cellular factors that mediate the PI3K pathway include PI3K, Akt, PDK-1, and others.

In an embodiment, the IκB degradation agonist is LPS, a highly potent stimulator of innate immunity. As shown in FIG. 1, LPS can bind to TLR4/CD14 receptors on human mononuclear cells and induces the formation and secretion of proinflammatory cytokines, such as TNF-alpha, MIF, IL-1~, IL-6, IL-8, IL-12, IL-15 and IL-18, various colony-stimulating factors, various lipid mediators, and reduced oxygen species. LPS consists of a lipid component, lipid A, and a polysaccharide unit covalently linked in the membrane domain. The polysaccharide region consists of the terminal O-specific chain, a substructure that comprises up to 50 repeating oligosaccharide units of usually two to eight monomers, and the core region, which is linked to the lipid A. The O-specific chain is characterized by extreme structural variability in different species. It is believed that the lipid A component of LPS is responsible for the biological activity described in the Examples below. The biological activity of LPS is modulated by variation of the acylation pattern of the lipid A. This activity ranges from an agonistic effect, such as occurs with most naturally occurring LPS variants (e.g., *Salmonella friedenau* or *Salmonella abortus equi*), to the antagonistic effect of the LPS variants of plant-symbiotic microorganisms or synthetic derivatives. A comprehensive description of LPS may also be found in A. Wiese, K. Brandenburg, U. Seydel, and S. Muller-Leoennies: The Dual Role of Lipopolysaccharide as Effector and Target Molecule. Biol. Chem., 380, pp. 767-784.

As shown in FIG. 1, in peripheral blood monocytes LPS induces two peaks of ERK phosphorylation (P-ERK), a first peak ("early" P-ERK) within about 2 to about 4 min of LPS activation and a second peak ("late" P-ERK) within about 7 to about 15 min. The timing of the "early" and "late" P-ERK may vary depending on the IκB degradation agonist and the concentration of the IκB degradation agonist. While the late P-ERK peak was found to be present in all samples, the presence and magnitude of the early P-ERK peak can be variable. As demonstrated in the Examples herein, proteasome inhibitors have been found to inhibit "late" P-ERK activation. In contrast, PI-3 kinase inhibitors have been found to inhibit "early" P-ERK but not "late" P-ERK. Thus, the sensitivity and specificity of the assays of the disclosure can be enhanced by including measurement of both IκB and P-ERK at the later time point.

Optimal incubation times and temperatures for each sample or target cell type with the IκB degradation agonist can be readily determined using routine experimentation. In at least one embodiment, the cells or sample is incubated with the IκB degradation agonist for about 1 min to about 60 min at a physiologically relevant temperature, such as 37° C. In some embodiments, the cells or sample is incubated with the IκB degradation agonist for about 1 min to about 45 min. In some embodiments, the cells or sample is incubated with the IκB degradation agonist for about 1 to about 15 minutes. During this period, early activating signal transduction pathway signaling proteins can be monitored. For example, as demonstrated in Examples of the disclosure, activation of P-ERK in monocytes of whole blood is typically measurable within about 2 minutes of exposure to the cells or sample to the IκB degradation agonist. As noted above, a second peak of P-ERK activation ("late" P-ERK) is generally observed in all samples, and occurs at about 7 to about 15 minutes, at about 8 to about 11 minutes, or about 9 to about 10 minutes, and detection of the second activation peak can be useful to increase the sensitivity and specificity of the assays of the disclosure.

D. Fixation and Permeabilization

Following activation of the cells or biological sample with the IκB degradation agonist, a portion of the cells or sample is removed at various incubation time points and then fixed to preserve intracellular and/or extracellular protein epitopes for subsequent detection. The fixation (or preservation) step generally includes contacting the cells or biological sample with a fixative in an amount sufficient to crosslink proteins, lipids, and nucleic acid molecules within the cells. The fixed cells are then permeabilized by contacting the fixed cells with a permeabilization reagent in an amount sufficient to lyse any red blood cells present in the sample and to permeabilize the target cells. To the extent that the sample does not contain red blood cells, i.e., the sample has been previously fractionated, it is understood that the lysis step may be unnecessary. In some embodiments, the fixation step may be before the addition of a proteasome effector to the biological sample for the purposes of establishing a control sample. The cells or sample can be fixed by any appropriate fixative agent useful for this purpose according to conventional methods. Examples of suitable fixative agents include but are not limited to aldehyde, formaldehyde, paraformaldehyde, formalin, glutaraldehyde, picric acid, ethanol, methanol, osmium tetroxide, potassium dichromate, chromic acid, potassium permanganate, and mixtures thereof. The fixative agent can be added either in concentrated solution or in diluted form to achieve the desired concentration. In embodiments, the concentration of the fixative agent can be between about 0.1 percent and about 20 percent v/v, between about 0.5 percent and about 15 percent v/v; between about 1 percent and about 10 percent v/v, between about 1 percent and about 8 percent v/v, between about 1 percent and about 4 percent v/v, or between about 1 percent and about 2 percent v/v. In an embodiment, the fixative comprises about 10% (v/v) formaldehyde.

The permeabilizer reagent typically includes a detergent component and is added in a final amount sufficient to achieve a concentration to lyse red bloods cells if present in the sample and permeabilize the cells of interest in the sample. For example, if the sample is a whole blood sample, an amount of the permeabilizer reagent sufficient to lyse the red blood cells and permeabilize the white bloods cells is added to the whole blood sample. The concentration of the detergent in the permeabilizer reagent can be selected by the user based on a variety of conditions and generally comprises a range of between about 0.1 percent and about 10 percent v/v; between about 0.1 percent and about 8 percent v/v; between about 0.1 percent and about 7 percent v/v; between about 0.1 percent and about 6 percent v/v; between about 0.1 percent and about 5 percent v/v; between about 0.1 percent and about 4 percent v/v; between about 0.1 percent and about 3 percent v/v; between about 0.1 percent and about 2 percent v/v; or between about 0.1 percent and about 1 percent v/v. The detergent can be an ionic or a non-ionic detergent. Suitable detergents are those that permeabilize cells and retain surface and/or intracellular epitope integrity. In some embodiments, the detergent is a non-ionic detergent. An exemplary non-ionic detergent is ethyoxylated octylphenol, which is referred to by the commercial name of Triton X-100®(Sigma T9284). Other useful permeabilizing reagents include octylphenoxypoly(ethyleneoxy)ethanol, commercially available as Igepal® CA-630 (Sigma N-6507) or Nonidet P-40 (NP-40) (Sigma), poly(oxyehtylene)cetyl ether, commercially available as Brij-58®, and linear alcohol alkoxylates, commercially available as Plurafac® A-38 (BASF Corp) or Plurafac® A-39 (BASF Corp). In some embodiments, fixation and permeabilization reagents are provided as a kit, such as PerFix-P®, PerFix-nc® or PerFix-Expose® (Beckman Coulter, Inc., Brea, Calif.), Intraprep® (Beckman Coulter. Inc.), Immunoprep® (Beckman Coulter, Inc.), or Versalyse® (Beckman Coulter, Inc.).

In some embodiments, the fixed and permeabilized cells are contacted with a denaturing agent, such as an alcohol, in an amount sufficient to unmask cellular epitopes, in particular intracellular epitopes that may be lost due to crosslinking in the fixation step. The alcohol treatment can help to preserve both extracellular and intracellular epitopes. The final concentration of alcohol can be adjusted by the user in length of incubation, temperature and concentration depending on the particular epitopes targeted for unmasking and measurement. The final alcohol concentration is generally between about 25 percent and about 75 percent v/v, between about 30 percent and about 70 percent v/v, between about 35 percent and about 65 percent v/v, between about 40 percent and about 60 percent v/v, or between about 45 percent and about 55 percent v/v. The alcohol is typically ethanol or methanol. In some embodiments, acetone can be substituted for the alcohol. In some embodiments, the sample can be contacted with the alcohol or acetone at a temperature, for example, about −30 degrees Celsius, about −20 degrees Celsius, about −10 degrees Celsius, about −5 degrees Celsius, about 0 degrees Celsius, about 4 degrees Celsius, about 6 degrees Celsius, about 8 degrees Celsius, or any other temperature that facilitates the unmasking of intracellular epitopes without reducing the reactivity of cell surface epitopes. In an embodiment, the cells are treated with about 50% methanol to unmask intracellular phospho-epitopes. Fixation and permeabilization methods and methods for unmasking of intracellular epitopes are further described in U.S. Pat. No. 7,803,523 B2, US2010/0086951, Chow et al., 2005 International Society for Analytical Cytology (2005), 5-17, Chow et al., Current Protocols in Cytometry (2008), 9.27.1-9.27.19, and Hedley et al., Recent Advances in Cytometry, Part B (2011), p 203-220.

E. Binding Agent

Phosphorylation is a transient, reversible event indicative of the activation status of signaling proteins. By measuring the phosphorylation state of proteins according to the assay methods of the disclosure, signaling cascades in response to activation of the sample with the IκB degradation agonist, or treatment of the sample with the proteasome effector, or a combination thereof can be determined. The degradation of IκB and/or phosphorylation (e.g., activation) of signal transduction molecules in the cells or sample can be detected with a binding agent or capture molecule. The cells or sample can be contacted with one or more binding agents following fixation and permeabilization. Alternatively, the fixed calls can be contacted concurrently with the permeabilization reagent and one or more binding agents.

The terms "binding agent" and "capture reagent" are used interchangeably herein. The binding agent or capture molecule can be any molecule or complex of molecules capable of specifically binding to a desired target, such as a protein, carbohydrate, or DNA, or a particular isoform or phosphorylated form of the target. The binding should be sufficient to remain bound under the conditions of the assay, including wash steps to remove non-specific binding. The binding target can be intracellular or extracellular. Examples of binding targets for use in the assay methods of the disclosure include but are not limited to IκB, ERF, P-ERK, Akt, P-Akt, S6, and P-S6. The binding agent or capture molecule can be a protein, small organic molecule, carbohydrates (including polysaccharides), polynucleotide, lipid, receptor, antibody, antibody fragment, and the like. The assay methods of the disclosure typically include one or more binding agents comprising antibodies or antibody fragments. Such antibodies include, but are not limited to, polyclonal, monoclonal, mono-specific polyclonal antibodies, antibody mimics, chimeric, single chain, Fab, Fab' and F(ab')$_2$ fragments, Fv, or scFv. Specific binding in the context of the present disclosure refers to a binding reaction which is determinative of the presence of a target protein in the presence of a heterogeneous population of proteins and other biological molecules. Thus, under designated assay conditions, the specified binding agents bind preferentially to a particular protein or isoform of the particular protein and do not bind in a significant amount to other proteins or other isoforms present in the sample. In some embodiments, the dissociation constants of the binding agent and binding target will be less than about $10^{-4}$-$10^{-6}$ M, with less than about $10^{-5}$ to $10^{-12}$ M being preferred and less than about $10^{-7}$-$10^{-12}$ M being particularly preferred.

The binding agent can also be a binding pair specific to the phosphorylated form of a protein. Such binding pairs are typically constructed using short phosphorylated peptide immunogens coupled to carrier proteins. Thus, detectable binding agents specific for different phospho-residues within the same signaling protein can be utilized in the methods provided by the invention, such that subsequent measurement provides insight into residues important for particular signaling events. Phospho-specificity can be confirmed by comparing resting versus stimulated cells, treating samples with phosphatases prior to analysis, competing with phosphorylated peptides versus non-phosphorylated ones, and normalizing phospho-protein levels to total protein content.

The binding agents can be specific for the activated (e.g., phosphorylated) form of a target protein, such as IκB or ERK. For example, activation state-specific binding agents can be used in the assay methods of the disclosure to identify distinct signaling cascades of a subset or subpopulation of complex cell populations; and the ordering of protein activation (e.g., kinase activation) in potential signaling hierarchies. In some embodiments, the assay includes a binding agent specific for IκB or a particular isoform thereof, including but not limited to IκBalpha, IκBbeta, IκBepsilon, IκBgamma, BCL3, p100, or p105. In some embodiments, the assay includes a binding agent that is specific for phosphorylated IκB. In some embodiments, the assay includes a binding agent specific for unphosphorylated IκB.

The assay of the present disclosure can be used to detect any particular protein isoform in a sample that is antigenically detectable and antigenically distinguishable from other isoforms of the proteins which are present in the sample. Antibodies, many of which are commercially available, have been produced which specifically bind to the phosphorylated isoform of a protein but do not specifically bind to a non-phosphorylated isoform of a protein. Exemplary antibodies for IκB include anti-IκB clone L35A5, which is commercially available from Cell Signaling Technologies. Exemplary antibodies for P-ERK include Phospho-p44/42 MAPK (Erk 1/2) clones E10 or D13.14.4E, which are commercially available from Cell Signaling Technologies. Exemplary antibodies for detecting P-Akt include antibodies that bind to Akt only when phosphorylated at Ser 473, which are commercially available from Cell Signaling Technologies. Exemplary antibodies for detecting P-S6 include antibodies that bind to S6 only when phosphorylated at Ser235/236, which are commercially available from Cell Signaling Technologies. Additional examples include but are not limited to monoclonal antibodies against phospho-TYK2 (Tyr1054/1055), phospho-p38 MAP kinase (Thr180/Tyr182), phospho-PKC-PAN substrate, phospho-PKA-substate, phospho-SAPK/JNK (Thr183/Tyr185), phospho-tyrosine (P-tyr-100), p44/42 MAPK, phospho-MEK 1/2 (Ser217/221), phospho-p90RSK (Ser381), p38 MAPK, JNK/SAPK, phospho-Raf (Ser259), phosphoElk-1 (Ser383), phospho-CREB (Ser133), phosphoSEK1/MKK4 (Thr261), phospho-Jun (Ser 63), phosphoMKK3/MKK6 (Ser189/207). AKT, phospho FKHR, FKHR, phospho-Gsk3 alp21, phospho-AFX, PARP, BAD, phospho-BAD Ser112, phospho-BAD Ser155, p2'7, p21, cFLIP. MYC, p53, NFκB, Ikkalpha, Ikkbeta, and phospho-tyrosine and phospho-threonine combination.

In some embodiments, the binding agent specifically binds a cellular surface antigen. The binding should be sufficient to remain bound under the conditions of the assay, and may include wash steps to remove non-specific binding. Examples of cellular surface antigens include transmembrane proteins, membrane associated proteins, receptors, membrane components, cell wall components, and other components of a cell accessible by an agent at least partially exterior to the cell. In some embodiments, a cellular surface antigen is a marker or identifier of a type or subtype of cell. For example, a particular surface antigen or combination of surface antigens can be useful as biomarker for a particular type of hematopoietic cell or subtype of cell. Cluster of differentiation (CD) molecules are useful cellular surface antigens for identifying or characterizing cells, including hematopoietic cells. CD molecules have been determined and characterized for hematopoietic cells, see for example bdbiosciences.com. A CD molecule or combination of CD molecules can be selected to specifically identity a particular cell type or subtype within the biological sample. In some embodiments, the cellular surface antigen comprises CD3, CD4, CD8, CD10, CD11a, CD14, CD15, CD16, CD19, CD20, CD24, CD25, CD30, CD31, CD34. CD38, CD45. CD53, CD56. CD61, CD91, CD114, CD117, CD138, CD182, or a combination thereof. Utilizing a combination of cellular surface antigen markers, multiple cell types or subtypes in the sample can be identified and distinguished. In some embodiments, the cellular surface antigen comprises a marker or identifier of monocytes. One example of a cellular surface antigen useful for identifying monocytes in a mixture of cells is CD14. Antibodies against CD14 and other monocyte specific antigens, such as the CD molecules described herein, are known. Exemplary antibodies for this purpose include, for example, CD14 clones 116, 322A-1, or RM052, which are commercially available from Beckman Coulter, Inc. (Miami, Fla.).

In some embodiments, the assay includes a binding agent to a cellular surface antigen that is a marker or identifier of lymphocytes. One example of a cellular surface antigen useful for identifying lymphocytes in a mixture of cells is CD3 and/or CD19. In some embodiments, the assay includes a binding agent to a cellular surface antigen that is a marker or identifier of eosinophils. In some embodiments, the assay includes a binding agent to a cellular surface antigen that is a marker or identifier of multiple myeloma cells. One example of a cellular surface antigen useful for identifying multiple myeloma cells in a mixture of cells is CD38/CD138. In some embodiments, the assay includes a binding agent to a cellular surface antigen that is a marker or identifier of a type of cancer cell. In some embodiments, the assay includes a binding agent to a cellular surface antigen that is a marker or identifier of an autoimmune disease causing cell. In some embodiments, the assay includes a binding agent to a cellular surface antigen that is a marker or identifier of an allergy associated cell. In some embodiments, the assay includes a binding agent to a cellular surface antigen that is a marker or identifier of a plasma cell.

The assay methods of the disclosure generally employ one or more binding agents that bind an activatable protein or phospho-epitope in combination with one or more binding agents that bind a cellular surface antigen. For example, a binding agent that binds IκB can be used in combination with a binding agent that binds P-ERK and a binding agent that binds CD14. In this way the degradation of IκB and phosphorylation of ERK in a monocyte can be detected and/or monitored. In an embodiment, a first plurality of binding agents that bind an activatable protein or phospho-epitope, wherein the first plurality includes binding agents directed to different activatable proteins or phospho-epitopes, is employed in combination with a second plurality of binding agents, wherein the second plurality includes binding agents directed to different cellular surface antigen, such that the different types or subtypes of cells present in a biological sample can be differentiated and independently analyzed.

The binding agents of the invention are typically labeled with a molecule that can be directly (i.e., a primary label) or indirectly (i.e., a secondary label) detected. The label can be visualized and/or measured or otherwise identified so that its presence or absence can be detected by means of a detectable signal. Examples of suitable labels include enzymes (e.g., horseradish peroxidase), particles (e.g., magnetic particles), fluorophores, chromophores, phosphorescence tags, chemiluminescence tags, specific binding partner pairs, and the like. Suitable binding partner pairs include, but are not limited to: antigens (such as proteins (including peptides) and small molecules) and antibodies (including fragments thereof (FAbs, etc.)); proteins and small molecules, including biotin/streptavidin; enzymes and substrates or inhibitors; other protein-protein interacting binding pairs; receptor-ligands; and carbohydrates and their binding partners. Nucleic acid-nucleic acid binding proteins pairs are also useful. Suitable binding partner pairs include, but are not limited to, biotin (or imino-biotin) and streptavidin, digeoxinin and Abs, and Prolinx™ reagents.

In a typical embodiment, the label is a fluorophore. The fluorophore may be a small molecule fluorophore or a proteinious fluorophore. Suitable fluorophores include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 Oregon green, green fluorescent protein (GFP), blue fluorescent protein (BFP), enhanced yellow fluorescent protein (EYFP). Additional fluorescent labels suitable for use in the assay methods of the disclosure include ALEXA FLUOR® dyes, such as ALEXA FLUOR® 350, ALEXA FLUOR® 430, ALEXA FLUOR® 488, ALEXA FLUOR® 546, ALEXA FLUOR® 568, ALEXA FLUOR® 594, ALEXA FLUOR® 633, ALEXA FLUOR® 660, and ALEXA FLUOR® 680. Multiple fluorescent labels can be employed with the binding agents. A combination of fluorophores can be selected based upon absorption/emission to provide for the visualization of a number of different cells types in a sample wherein each cell type can be specifically identified by a particular fluorescent label. In some embodiments, at least two fluorescent labels are used which are members of a fluorescence resonance energy transfer (FRET) pair. FRET pairs (donor/acceptor) useful in the invention include, but are not limited to, EDANS/fluorescein, IAEDANS/fluorescein, fluorescein/tetramethylrhodamine, fluorescein/LC Red 640, fluorescein/Cy 5, fluorescein/Cy 5.5, and fluorescein/LC Red 705.

For embodiments employing flow cytometry, cells expressing an epitope bound by a labeled binding agent can be identified by the signature fluorescent signal emitted by the fluorophore label when excited by laser light of the proper wavelength. Preferred fluorophores for flow cytometry include phycobiliproteins B-phycoerythrin (B-PE), R-phycoerythrin (R-PE) and allophycocyanin (APC), which are suitable for applications that require either high sensitivity or simultaneous multicolor detection. If desired, tandem conjugates containing two labels, for example, a phycoerythrin-labeled binding reagent in combination with a green-fluorescent detection reagent, can be used to detect two different signals using simultaneous excitation with the spectral line of the instrument laser. If desired, activity-based labels can be designed and synthesized that consist, for example, of alpha-bromobenzylphosphonate as a phosphatase-specific trapping device and a linker that connects the trapping device with a biotin tag for visualization and purification as described by Kumar et al., Proc. Natl. Acad. Sci., USA 101:7943-48, (2004).

When selecting fluorophore labels for use in flow cytometry, the fluorophore label's absorbance spectrum must match the laser line used in the cytometer and its emission must fall within detection filter sets. In addition, the label cannot interfere with the binding agent, for example, antibody binding characteristics or permeability through the cell structure. It is understood that large protein fluorophores like PE or APC may slow antibody entry into cells and affect its binding characteristics. Small molecule labels, for example, fluorophores such as FITC, ALEXA FLUOR® 488, and ALEXA FLUOR® 647 can provide desirable staining characteristics providing proper control of fluorophore-to-protein ratios. Extensive discussion of fluorophore uses and applications in flow cytometry can be found, for example, in Petit et al., Biol. Cell, 78:1-13, 1993; Mullins, Methods Mol. Biol., 34: 107-16 (1994); and Shapiro. Methods Cell Biol., 63:107-29, 2001.

Conjugation of the label to the binding agent can be performed using conventional procedures. See, for example, O'Sullivan et al., 1981, "Methods for the Preparation of Enzyme-antibody Conjugates for Use in Enzyme Immunoassay," in Methods in Enzymology, Langone and Van Vunakis, Eds., Vol. 73 (Academic Press, New York, N.Y.), pp. 147-166. Conventional methods are available to bind the label covalently to proteins or polypeptides. For example, coupling agents such as dialdehydes, carbodiimides, dimaleimides, bis-imidates, bis-diazotized benzidine, and the like, can be used to label antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., Nature, 144:945 (1962): David et al., Biochemistry, 13:1014-1021 (1974); Pain et al., J. Immunol. Methods, 40:219-230 (1981); and Nygren J., Histochem, and Cytochem., 30:407-412 (1982). Fluorescent or chemiluminescent labels can be used to increase amplification and sensitivity to about 5-10 pg/mL, or better.

In certain embodiments, a secondary detectable label is used. A secondary label is one that is indirectly detected. For example, a secondary label can bind or react with a primary label for detection, can act on an additional product to generate a primary label (e.g. enzymes), etc. Secondary labels include, but are not limited to, one of a binding partner pair; chemically modifiable moieties; nuclease inhibitors, enzymes such as horseradish peroxidase, alkaline phosphatases, luciferases, etc. In an embodiment, the secondary label is a chemically modifiable moiety. In this embodiment, labels comprising reactive functional groups are incorporated into the molecule to be labeled. The functional group can then be subsequently labeled (e.g., either before or after the assay) with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers such as homo- or hetero-bifunctional linkers.

In certain embodiments, the binding of an activation state-specific binding agent to a corresponding isoform of a target activatable protein is indicative of the identity of the activatable protein and of its activation state. In some embodiments, the activation state-specific binding agent is a peptide comprising a recognition structure that binds to a target structure on an activatable protein. A variety of recognition structures are well known in the art and can be made using methods known in the art, including by phage display libraries. In a certain embodiment, the activation state-specific binding agent comprises the following recognition structure: SKVILFE-random peptide loop-SKVILFE. Binding agents having such recognition structures can bind with high affinity to specific target structures.

F. Assay Systems

The binding of a binding agent to a desired target according to the assay methods of the disclosure can be detected and quantified with an immunoassay. Examples of immunoassays include, but are not limited to, fluoroluminescence assay (FLA), chemiluminescence assay (CA), enzyme-linked immunosorbant assay (ELISA), flow cytometry and the like. The immunoassay, in one embodiment, can be designed for an automated, high throughput instrument. For example, the Access, family of instruments by Beckman Coulter, Inc. (Brea, Calif.) are well suited for the assay methods of the disclosure. The Access® Immunoassay System allows for rapid throughput of up to 100 tests per hour through the use of a reaction vessel loader that has the capacity for up to 3 hours of continuous sample processing.

Preferred assay methods of the disclosure utilize flow cytometry or laser scanning cytometry. The use of flow cytometry, particularly polychromatic flow cytometry, permits the multi-dimensional analysis and functional assessment of the signaling pathway in single cells. Flow cytometry devices and protocols have also been described in numerous publications. See, for example, Flow Cytometry and Sorting, 2.sup.nd ed. (1990) M. R. Melamed et al., eds. Wiley-Liss; Flow Cytometry and Cell Sorting, 2.sup.nd ed. (2000) A. Radbruch, Springer-Verlag; and In Living Color: Protocols in Flow Cytometry and Cell Sorting (2000) Diamond and Demaggio, eds. Springer-Verlag. Flow cytometry methods are also described in U.S. Pat. Nos. 5,968,738 and 5,804,387. Flow cytometers are commercially available, for example, from Beckman Coulter, Inc. (Brea, Calif.) and BD Biosciences (San Jose, Calif.). Examples of suitable flow cytometers for use in the method include but are not limited to GALLIOS™, CyAn ADP Analyzer, Coulter Epics, Coulter Epics XL, Coulter XL MCL. FC 500, FC 500 MCL, FC 500 MPL, FACSCalibur, FACSCanto, FACSCount, and FACSAria.

A flow cytometer that is capable of multicolor analyses, for example, 2, 4, 6, 8, or more different colors, can be employed and provides for the analysis of multiple, distinct intracellular epitopes in combination with one of more distinct cellular surface antigens. In this manner, the simultaneous monitoring of IκB levels and one or more signaling cascades in a particular cell type or subtype in a heterogeneous or homogenous sample can be achieved to determine and/or monitor the effect of a particular proteasome effector on proteasome activity in a desired cell population after the addition of IκB degradation agonist. For example, a peripheral whole blood sample can be contacted with a first labeled binding agent that binds IκB, a second labeled binding agent that binds a cellular surface antigen, such as CD14, and optionally a third labeled binding agent that binds an activatable protein, such as Erk. Akt, p38, S6, or SAPK, to determine and/or monitor proteasome activity in monocytes in the whole blood sample. It is understood that several signaling cascades or members of one particular cascade can be analyzed simultaneously with the degradation of IκB based on the detectable binding agents selected. Specific subsets of cells can also be identified within a complex population of cells, such as a whole blood sample, based on forward scatter, side scatter, a combination of forward scatter and side scatter, or a combination of forward scatter or side scatter and one or more detectable cellular surface antigens such that the degradation of IκB can be monitored simultaneously within multiple, distinct subsets of cells (such as monocytes, lymphocytes, and granulocytes) within the complex population of cells.

G. Kits

As a matter of convenience, the methods of the disclosure can be provided in the form of a kit. Such a kit is a packaged combination form comprising one of more reagents for use in the methods and instructions for performing the methods of the disclosure. In a typical embodiment, the kit includes an IκB degradation agonist; a binding agent that specifically binds an IκB protein (e.g., phosphorylated, unphosphorylated, or both), and instructions on how to perform the method using these reagents. The binding agent may be labeled or unlabeled. If unlabeled binding agent is provided in the kit, the user would select a particular label and conjugate the label to the binding agent before using the binding agent in an assay. The kit may optionally include reagents for conjugating a label to the binding agents.

The kit can further include one of more binding agents that specifically bind an activatable protein, such as ERK. Akt, S6, p38, and SAPK, or activated (e.g., phosphorylated) form thereof and/or one or more binding agents that specifically bind a cellular surface antigen. The binding agents may be labeled or unlabeled. If unlabeled binding agent is provided in the kit, the user would select a particular combination of labels to distinguish, for example, a first binding agent that binds IκB, a second binding agent that binds cellular surface antigen, and optionally a third binding agent that binds an activatable protein and then conjugates the selected label to the particular binding agents before using the binding agents in an assay. The kit may optionally include reagents for conjugating a label to the binding agents and/or instructions for conjugating a label to the binding agents.

In further embodiments, the kit may include a fixative agent as described herein, a permeabilizing agent as described herein, a denaturing agent as described herein for unmasking epitopes, one of more incubation buffers, one or more staining buffers, and/or one or more labeling agents as described herein for labeling one of more of the binding agents. In further embodiments, the kit can include one or more control cell populations and/or one or more proteasome effectors for use as a positive or negative control for aid in determining and/or monitoring proteasome activity. In a preferred embodiment, the kit comprises an IκB degradation agonist, a first labeled binding agent that specifically binds an IκB protein, a second labeled binding agent that specifically binds a cellular surface antigen, and optionally a third labeled binding agent that specifically binds a phosphorylated signaling protein, such as P-ERK, P-S6. P-Akt, P-p38, or P-SAPK.

H. Uses

The assay methods of the disclosure are useful for measuring proteasome activity in cells and determining and/or monitoring the effects of a proteasome effector, such as a proteasome inhibitor, on proteasome activity. Utilizing flow cytometry as described herein, the proteasome activity in specific cell populations within a mixture of different cell types can be measured simultaneously. A method of detecting proteasome activity in a target cell is provided. The method typically includes: contacting a biological sample as described herein containing one or more target cells with an IκB degradation agonist as described herein to activate target cells in the biological sample; terminating the action of the IκB degradation agonist by contacting the biological sample with a fixation and/or permeabilization reagent; contacting the biological sample with a first labeled binding agent as described herein capable of binding IκB following activation of the target cells with the degradation agonist; and detecting as described herein the amount of first labeled binding agent bound to a target cell in the biological sample, thereby detecting proteasome activity in the target cell. The method can further include contacting the biological sample with a proteasome effector and subsequently contacting the biological sample with the IκB degradation agonist. The target cell can be any cell in which it is desirable to determine and/or monitor proteasome activity. In an embodiment, the target cell is a hematopoietic cell. In another embodiment, the target cell is a neoplastic cell. In a further embodiment the neoplastic cell is a cancer cell.

The assay method can further include one or more centrifugation steps. As exemplified herein, a first centrifugation step for removing the permeabilization agent can be performed prior to the contacting the fixed and permeabilized cells with binding agents. In addition, a further centrifugation step can be performed after contacting the permeabilized cells with the alcohol to remove the alcohol. It is understood that washing steps and resuspension in appropriate buffer, for example, phosphate buffered saline (PBS), can be performed at various steps of the method as desired by the user. Suitable buffers are exemplified herein and further described in Chow et al., 2005 International Society for Analytical Cytology (2005), 5-17, Chow et al., Current Protocols in Cytometry (2008). 9.27.1-9.27.19, and Hedley et al., Recent Advances in Cytometry, Part B (2011), p 203-220.

In certain embodiments, the biological sample includes one or more of lymph, spleen cells, peripheral blood mononuclear cells, white blood cells, or bone marrow cells. In an embodiment, the biological sample is a peripheral whole blood sample. In embodiment, the hematopoietic cell comprises a leukocyte. In a further embodiment, the leukocyte is a monocyte. In a further embodiment, the leukocyte is a lymphocyte. The biological sample can also include neoplastic or disease associated cells, such as tumor or cancer cells. In certain embodiments, the biological sample is from a patient. The patient may have or may not have a disease or disorder, such as cancer, allergy, or an autoimmune disease. The cancer may be leukemia, lymphoma, myeloma, solid tumor, breast cancer, pancreatic cancer, colon cancer, or non-small cell lung cancer.

In an embodiment, the proteasome effector is a proteasome inhibitor. In a further embodiment, the proteasome inhibitor is a non-covalent proteasome inhibitor, a reversible covalent proteasome inhibitor, or an irreversible covalent proteasome inhibitor. In a further embodiment, the proteasome inhibitor is selected from bortezomib, disulfiram, epigallocatechin-3-gallate, salinosporamide A, carfilzomib, ONX-0912, CEP-18770, MLN-9708, MG-132, MG-262, PR-171, marizomib, PSI, tyropeptin A, fellutamide B, MLN-2238, epoxomicin, eponemycin, lactacystin, alpha-ketoaldehydes, omuralide, PS-519, belactosin A, NIP-$L_3$VS, MV151, syringolin A, glidobactin A, TMC-95, TMC-95A, argyrin A, scytonemide A, scytonemide B, capped dipeptide 1, ritonavir, benzylstatine peptide 1, capped dipeptide 2, 5-methoxy-1-indanone-dipeptide benzamide, CVT-659, PI-083, thiostrepton, siomycin, green-tea polyphenol, triterpenoid, PR-39, 5-amino-8-hydroxyquinoline, NC-005, NC-005-VS, YU-101, LU-005, YU-102, NC-001, LU-001, NC-022, PR-957 (LMP7), CPSI (beta5), LMP2-sp-ek, IPSI-001 (LMP2), BODIPY-NC-005-VS. BODIPY-NC-001, or azido-NC-002.

The IκB degradation agonist can be a pan-kinase activator. A pan-kinase activator is an agonist that activates a broad spectrum of kinases in a cell with little selectivity. In an embodiment, the IκB degradation agonist is a TLR4 agonist. In a further embodiment, the IκB degradation agonist is LPS, CD40L, PMA, TGF, anti-CD28, anti-CD3/CD28 or TNF-alpha. In an embodiment, the first labeled binding agent specifically binds IκBalpha, IκBbeta, IκBepsilon, IκBgamma, BCL3, p100, or p 105. In another embodiment, the first labeled binding agent specifically binds a phosphorylated form of an IκB.

For establishing baseline proteasome activity of hematopoietic cells in a biological sample or control sample, the amount of IκB degradation can be determined for a biological sample that has not been contacted with the proteasome effector. For example, IκB degradation after induction by IκB degradation agonist in specific cell populations within a biological sample that has been pretreated with the proteasome effector can be compared to the same cell populations in a biological sample that has not been contacted with the proteasome effector to determine, measure, and/or monitor the effect of the proteasome effector on proteasome activity in the specific cell populations. Accordingly, a protcasome effector may be determined to be a proteasome inhibitor when the amount of first labeled binding agent bound to a hematopoietic cell is increased in a cell contacted with the proteasome effector relative to the same type or subtype of cell not contacted by the proteasome effector or contacted with less of the proteasome effector.

In certain embodiments, the control sample is a biological sample from a patient that has been contacted with less of the proteasome effector relative to a test sample. In other embodiments, the control sample is a biological sample from a patient that has not been contacted with the IκB degradation agonist and/or proteasome effector. In yet other embodiments, the control sample is a biological sample from a normal, healthy subject. Detecting an increased level of the first labeled binding agent bound to a target cell, such as a hematopoietic cell or neoplastic cell, in a test sample relative to the control sample is indicative of the proteasome effector being a proteasome inhibitor. In some embodiments, the method includes obtaining one or more additional (e.g. a third, fourth, fifth, etc.) target cell containing test samples (e.g., biological samples) and screening these samples for proteasome activity according to the method for comparative purposes.

If the biological sample is from a patient suffering from a disease or disorder, such as cancer, the effects of therapy comprising a proteasome effector, such as a proteasome inhibitor, can be evaluated according to the method on proteasome activity and other cellular processes in target cells (e.g., cancer cells) and non-target cells (e.g., non-cancer cells) in the biological sample and allows the clinician to monitor treatment and adjust to therapeutic regimen based on the effects in an individual patient. For example, if proteasome activity of non-target (e.g., non-cancer cells, non-disease related cells, non-autoimmune associated cells, or non-allergy related cells) is being adversely affected by the treatment regimen or dosage at an unacceptable level, the regimen or dosage may be adjusted to decrease adverse effects on non-target cells while maintaining a suitable level of proteasome inhibition to kill the target cells.

Detecting the amount of first labeled binding agent bound to the target cell in the biological sample can include measuring the mean fluorescent intensity (MFI) of the biological sample, electronic impedance of the biological sample, the optical scatter of the biological sample, or contacting the biological sample with a second labeled binding agent that specifically binds the target cell. For example, the method can include: contacting a biological sample containing one or more target cells with a proteasome effector; subsequently contacting the biological sample with an IκB degradation agonist; terminating IκB degradation agonist action with fixation/permeabilization reagent; contacting the biological sample with a first labeled binding agent capable of binding IκB following activation of the target cells with the degradation agonist; contacting the biological sample with a second labeled binding agent that is capable of binding a target cell; and detecting the amount of first labeled binding agent bound to a target cell and the amount of the second labeled binding agent bound to a target cell.

The biological sample can be contacted with the second labeled binding agent before, simultaneous, or subsequent to the contacting the biological sample with the first labeled binding agent. In certain embodiments, the second labeled binding agent specifically binds a subtype of hematopoietic cell or neoplastic cell. In some embodiments, the subtype of hematopoietic cell is selected from granulocytes, neutrophils, eosinophils, basophils, lymphocytes, monocytes, macrophages, dendritic cells. B cells, T cells, or natural killer cells. In certain embodiments, the second labeled binding agent is directed to a cellular surface antigen and is utilized alone or in combination with additional labeled binding agents to other cellular surface antigens to provide a marker for identifying a particular cell type or subtype within the biological sample. In some embodiments the subtype of leukocyte consists of monocytes and lymphocytes. The subtype of leukocyte may be monocytes. The subtype of leukocytes may be lymphocytes. The subtype of leukocytes may be CD19+ cells. In some embodiments, the cellular surface antigen is selected from the group consisting of CD3, CD4, CD8, CD10, CD11a, CD14, CD15, CD16, CD19, CD20, CD24, CD25, CD30, CD31, CD34, CD38, CD45, CD53, CD56, CD61. CD91, CD114, CD117, CD138, and CD182. In some embodiments, the cellular surface antigen is a marker or identifier of monocytes. The cellular surface antigen may be a marker or identifier of lymphocytes. In some embodiments, the cellular surface antigen is a marker or identifier of eosinophils. In some embodiments, the cellular surface antigen is a marker or identifier of a type of cancer, such as multiple myeloma. In an embodiment, the second labeled binding agent is an antibody that specifically binds target cancer cells. For example, in a biological sample from a patient with multiple myeloma the second labeled binding agent can be an antibody that specifically binds CD45 or CD38. Exemplary antibodies for this purpose include, CD45 clones J.33, KC56, or Immu19.2; CD38 clones T16, or LS198-4-3, CD34 clones Immu133, or QBEnd10, or 581; CD10 clones J5, or ALB 1; CD19 clones 89B, or J4.119; CD16, clone 3G8, and CD3, clones UCHT1 or HIT3a, which are commercially available from Beckman Coulter, Inc. (Brea, Calif.). The cellular surface antigen may be a marker or identifier of an autoimmune disease causing cell. In some embodiments, the cellular surface antigen is a marker or identifier of an allergy causing cell. The cellular surface antigen may be a marker or identifier of a plasma cell.

If the binding target for the second labeled binding agent is extracellular, the biological sample can be contacted with the second labeled binding agent before the cells are fixed and/or permeabilized as described herein. Suitable cellular surface antigens are described herein. As the IκB is an intracellular binding target, the biological sample is typically fixed as described herein with a fixative agent before contacting the biological sample with the first labeled binding agent. The fixed biological sample can be contacted with the first labeled binding agent concurrently or subsequent to permeabilization of the fixed biological sample with a permeabilizing agent as described herein.

The method can further include contacting the biological sample with one or more third labeled binding agents and detecting the amount of third labeled binding agent bound to the target cell. Typically, the third labeled binding agent is directed to intracellular binding targets, such as activatable signaling proteins including but not limited to ERK, Akt, p38, SAPK, or S6 in phosphorylated form. The biological sample is typically contacted with the fixative agent before contacting the biological sample with the third labeled binding agent(s). The fixed biological sample is generally contacted with the third labeled binding agent(s) concurrently or subsequent to permeabilization of the fixed biological sample with the permeabilizing agent. The biological sample is typically contacted with the third labeled binding agent concurrently with the first labeled binding agent, although the biological sample can be contacted with the first and third labeled binding agents independently if desired. The binding agent of the first, second, or third labeled binding agent can be an antibody or fragment thereof as described herein. In an embodiment, the antibody is a polyclonal antibody, monoclonal antibody, mono-specific polyclonal antibody, chimeric antibody, single chain antibody, human antibody, humanized antibody, Fab, Fab', F(ab')$_2$, Fv, or scFv.

In embodiments employing first, second, and third labeled binding agents as described herein, one or more target cells, such as hematopoietic or neoplastic cells, in the biological sample can be characterized by one of the following possible binding patterns: (1) first, second, or third labeled binding agent; (2) first and second labeled binding agents; (3) first and third labeled binding agents; (4) second and third labeled binding agents; or (5) first, second, and third labeled binding agents. These specific binding patterns allow for the simultaneous comparison of multiple cell populations within the biological sample being analyzed. In preferred embodiments, the binding of the labeled binding agents is detected by a particle analyzer, such as a flow cytometer. Flow cytometers are commercially available, for example, from Beckman Coulter, Inc. (Brea, Calif.) and BD Biosciences (San Jose, Calif.). Examples of suitable flow cytometers for use in the method include but are not limited to GALLIOS™, CyAn ADP Analyzer, Coulter Epics, Coulter Epics XL, Coulter XL MCL, FC 500, FC 500 MCL, FC 500 MPL, FACSCalibur, FACSCanto, FACSCount, and FACSAria.

In the method, the binding agents (e.g., first, second, and third binding agents) are preferably independently labeled with a detectable moiety as described herein, such as a fluorophore. In selecting the label moiety for a particular binding agent, the fluorescent emission spectra of the label moiety must be considered relative to the other label moieties employed in the method. Preferably, the selected label moiety comprises a unique fluorescent emission spectra or unique fluorescent emission spectrum frequency (wavelength) compared to the other label moieties. In some embodiments, each fluorophore is independently selected from hydroxycoumarin, methoxycoumarin, ALEXA FLUOR®, aminocoumarin, Cy2, FAM, ALEXA FLUOR® 488, Fluorescein FITC, ALEXA FLUOR® 430, ALEXA FLUOR® 532, HEX, Cy3, TRITC. ALEXA FLUOR®546, ALEXA FLUOR® 555, R-phycoerythrin, Rhodamine Red-X, Tamara, Cy3.5, Rox, ALEXA FLUOR® 568, Red 613, Texas Red, ALEXA FLUOR® 594, ALEXA FLUOR® 633, Cy5, ALEXA FLUOR® 660, Cy5.5, TruRed, ALEXA FLUOR® 680, Cy7, Pacific Blue, ALEXA FLUOR® 405, Pacific Orange, Qdot 525, Qdot 565, Qdot 585, Qdot 605, Qdot 655, Qdot 705, Qdot 800, RPE-Texas Red, RPE ALEXA FLUOR® 610, TRI-COLOR, RPE-ALEXA FLUOR® . 700, RPE-Cy5.5, RPE-Cy7, ALEXA FLUOR® 647, ALEXA FLUOR® 700, APC-ALEXA FLUOR® 750. PerCP, Fluorescein. APC-Cy7, APC-ALEXA FLUOR® 750, AmCyan, ALEXA FLUOR® 350, APC-Cy5.5, CyChrome, or PC5.

The laser spectra and detection filter sets should be considered when selecting the particular label moieties for use in the method. The selected label moieties should be compatible with the laser and detection filter sets and have a fluorescent emission spectra or fluorescent emission spectrum frequency (wavelength) that allows for discrimination between the different label moieties utilized in the method such that the fluorescence emission spectra or spectrum frequency of a first label moiety can be detected independently of the fluorescence emission spectra or spectrum frequency of a second label moiety, or of second and third label moieties, or of second, third, and fourth label moieties, etc.

The method can be used to screen candidate compounds, drugs or biomolecules for proteasome inhibitory activity to identity proteasome inhibitors for treating a disease or disorder, such as cancer. In an embodiment, the method comprises contacting a biological sample including one or more target cells, such as hematopoietic cell or neoplastic cell, with a candidate proteasome effector; subsequently contacting the biological sample with an IκB degradation agonist as described herein to activate target cells in the biological sample; terminating IκB degradation agonist action with fixation and/or permeabilization reagent, contacting the biological sample with a first labeled binding agent as described herein capable of binding IκB following activation of the target cells with the degradation agonist; detecting as described herein the amount of first labeled binding agent bound to a target cell in the biological sample; and comparing the amount of first labeled binding agent bound to the target cell in biological sample to a control sample, wherein a difference in the amount of first labeled binding agent bound to a target cell in the biological sample compared to the control indicates the composition is a proteasome effector. A proteasome effector is identified as a proteasome inhibitor when the amount of the first labeled binding agent bound to the target cell in the biological sample is greater than the amount of first labeled binding agent bound to a control target cell not contacted by the proteasome effector or contacted with less of the proteasome effector.

In an embodiment, the biological sample can include cancer cells, either from a patient or cell line. The biological sample can comprise purified cells or a combination of one or more purified cells types to evaluate proteasome activity in particular types or subtypes of cells under controlled conditions. In certain embodiments, the method includes analysis of a plurality of biological samples, which may include a plurality of samples from patients and/or tumor or cancer cell lines. In this way, a candidate compound, drug, or biomolecule can be screened for proteasome inhibitory activity according to the method across a broad range of clinically relevant samples. The plurality of biological samples may be compared against each other and/or against control samples as described herein to determine proteasome activity.

The method also provides for analysis of the kinetics of proteasome modulation by the proteasome effector. For a particular effector, the kinetics of proteasome modulation in test samples can be compared to reference values for kinetics of proteasome activity or modulation in control samples. In an embodiment, such a method includes detecting mean fluorescence intensity (MFI) of a population of cells bound to the first and/or second and/or third and/or additional labeled binding agents. In another embodiment, the method includes detecting the presence of individual cells in a population of cells, which are bound to the first and/or second and/or third and/or additional labeled binding agents. In yet another embodiment, the method includes detecting the percentage of total cells of a population (or subpopulation) bound to one or more labeled binding agents.

The method also provides for detecting modulation of proteasome activity in a patient by determining proteasome activity in a biological sample obtained from the patient before and after treatment with the proteasome effector. The biological sample can be a sample, such as peripheral blood, bone marrow, or ascities, from a cancer patient. The sample may be a biological sample from a cancer patient treated with a proteasome inhibitor. In an embodiment, the proteasome inhibitor is Bortezomib, carfilzomib, or ixazomib. In an embodiment, the method comprises obtaining a first biological sample comprising one or more target cells, such as a hematopoietic cell or neoplastic cell, from a patient prior to administration of the proteasome effector to the patient; obtaining a second biological sample comprising a target cell from the patient following the administration of the proteasome effector to the patient; contacting the first and second biological samples with an IκB degradation agonist as described herein to activate target cells in the biological sample; terminating IκB degradation agonist action in the first and second biological samples with a fixation and/or permeabilization reagent, contacting the first and second biological samples with a first labeled binding agent as described herein that is capable of binding IκB; detecting a target cell in each of the first and second biological samples; and determining the amount of first labeled binding agent bound to the detected target cell in each sample as described herein. A difference in the amount of the first labeled binding agent bound to the detected hematopoietic cell in each of the first and second biological samples is indicative of modulation of proteasome activity. In an embodiment, detecting the target cell in the first or second biological sample comprises measuring the MFI of the first or second biological sample with a particle analyzer, such as a flow cytometer, or contacting the first or second biological sample with a second labeled binding agent as described herein that binds the target cell in the first or second biological sample.

The amount of proteasome effector administered to the patient can be modified according to the results of the method. For example, if the proteasome effector is a proteasome inhibitor and the desired level of proteasome inhibition is not achieved in a biological sample from the patient, the amount of proteasome inhibitor administered to the patient in a subsequent administration can be increased to achieve the desired level of proteasome inhibition in the patient. In such an example, the amount of the first labeled binding agent bound to the detected target cell, such as a hematopoietic cell or neoplastic cell, in a biological sample obtained from the patient following the first administration of the proteasome inhibitor is compared to the amount of the first labeled binding agent bound to the detected target cell in a biological obtained the patient following the second administration of the proteasome inhibitor to determine the proteasome modulating effect of the second administration. Conversely, the amount of the proteasome inhibitor administered to the patient can be reduced if the dosage is toxic to the cells and/or the desired level of proteasome inhibition can be achieved with a lower dose. In an embodiment, the method includes obtaining one or more additional (e.g., a third, fourth, fifth, etc.) samples from the patient following a third, fourth, fifth, etc. administration of the proteasome effector to the patient. In another embodiment, the method includes determining the kinetics of proteasome modulation by the proteasome effector as described herein and comparing the kinetics of proteasome modulation to reference values for kinetics of proteasome activity or modulation from control samples as described herein. In an embodiment, the control samples can include a plurality of biological samples, optionally from a plurality of patients. The plurality of samples can include samples from patients having the same disorder and being administered the same proteasome effector at similar and/or different doses and/or biological samples from normal, healthy subjects.

EXAMPLES

The following examples are offered to illustrate, but not to limit the claimed invention.

Example 1

IκB as a Biomarker for Proteasome Activity in Peripheral Blood Cells

A flow-cytometry based assay to monitor proteasome activity in target cells has been developed. As shown in FIG. 1, exposure of cells (e.g., peripheral blood monocytes) to an activator of a signal transduction activator (e.g., LPS) results in phosphorylation of IκB via the TLR4 receptor. IκB normally sequesters the NF-κB complex in the cytoplasm and phosphorylation of IκB results in its ubiquination, tagging it for destruction by the proteasome. We have discovered that IκB levels can conveniently be used to monitor proteasome activity in peripheral bloods cells, providing for the development of a flow cytometry assay useful for monitoring and/or measuring the effect of drugs on proteasome activity.

Method

The assay generally comprises treating whole blood with an IκB degradation agonist and/or proteasome effector, fixing the blood cells, permeabilizing the fixed bloods cells, treating the fixed and permeabilized cells with an alcohol treatment to unmask intracellular phosphor-epitopes, and then staining the treated cells with antibodies for flow cytometry analysis.

Whole blood samples from normal human donors were collected. 100 μL aliquots of the whole blood were inserted into the bottom of 12×75 mm tubes. In order to reduce the potential for contamination of the sample with unfixed cells, blood was removed from the side of the tubes with a cotton swab. 1-2 μL of a proteasome effector was added to a first portion of the tubes and these tubes were incubated for 2 hours at 37° C. in a water bath. In this example, the proteasome effector was Bortezomib or MG-132, both proteasome inhibitors. Following pretreatment with the proteasome effector, 2 μL of 50 mg/mL stock solution (100 ng) of an IκB degradation agonist was added to the tubes and the tubes were incubated from 1 minute to 60 minutes at 37° C. in a water bath. In this example, the agonist was lipopolysaccharide (LPS). A second portion of the tubes were treated with the IκB degradation agonist and no proteasome effector. 2 μL of an IκB degradation agonist was added to these tubes and the tubes were incubated from 1 minute to 60 minutes as described above. For control tubes, 2 μL of phosphate buffered saline (PBS) was added to the tubes and the tubes were incubated as described above.

Following incubation, the cells were fixed and permeabilized with a PerFix-P® kit (Beckman Coulter, Inc., Brea. Calif.) according to the manufacturer's instructions. The fixed and permeabilized cells were then washed with 2 mL of Wash Buffer (PBS (w/o Ca++/Mg++) with 2% fetal bovine serum (FBS), sterile filtered (0.22 μm filter)) in the tubes and centrifuged at 500×g for 4 minutes. The cell pellet was resuspended in 2 mL of cold (4° C.) Wash Buffer, centrifuged at 500×g for 4 minutes, and the supernatant was aspirated.

Following the above wash steps, the fixed and permeabilized cells were resuspended in 100 μL of cold Wash Buffer comprising antibodies to specific intracellular antigens (e.g., signaling targets including P-ERK, P-Akt, P-p38, P-SAPK, P-S6, and antibodies to IκB). The antibodies were labeled with different fluorochromes (e.g. fluorophores) to facilitate their-individual measurement of the intracellular antigens. In order to target specific cell populations in the assay, antibodies capable of differentiating cell populations within the blood sample were also included in some of the tubes. For example, anti-CD14 antibodies were included to specifically label monocytes, anti-CD3 antibodies or anti-CD19 antibodies were included to specifically label T or B-cells respectively, and/or anti-CD38/CD138 antibodies were included to specifically label plasma cells. The cells were incubated with the antibodies for 30 minutes at room temperature and then the cells were washed in 2 mL of cold Wash Buffer and centrifuged as described above. The supernatant was aspirated and the cell pellet was resuspended in 350 μL of Resuspension Buffer (PerFix-P® kit) and analyzed on a flow cytometer (GALLIOS™) using a protocol with defined population gates and series of dual parameter histograms. A CD45-KO vs. SS dual parameter histogram was collected and a gate around the leukocyte population based on the CD45+ fluorescence and SS characteristics was drawn to exclude debris (CD45 negative events). A minimum of 2,500 CD14+ events were collected. A stop count region was set from the CD14-PC7 vs. SS histogram gated on monocytes. Dual parameter histograms gated on the appropriate populations were created to measure the populations of interest. The collected flow cytometric data was analyzed using KALUZA™ software.

Results

Figure 2:
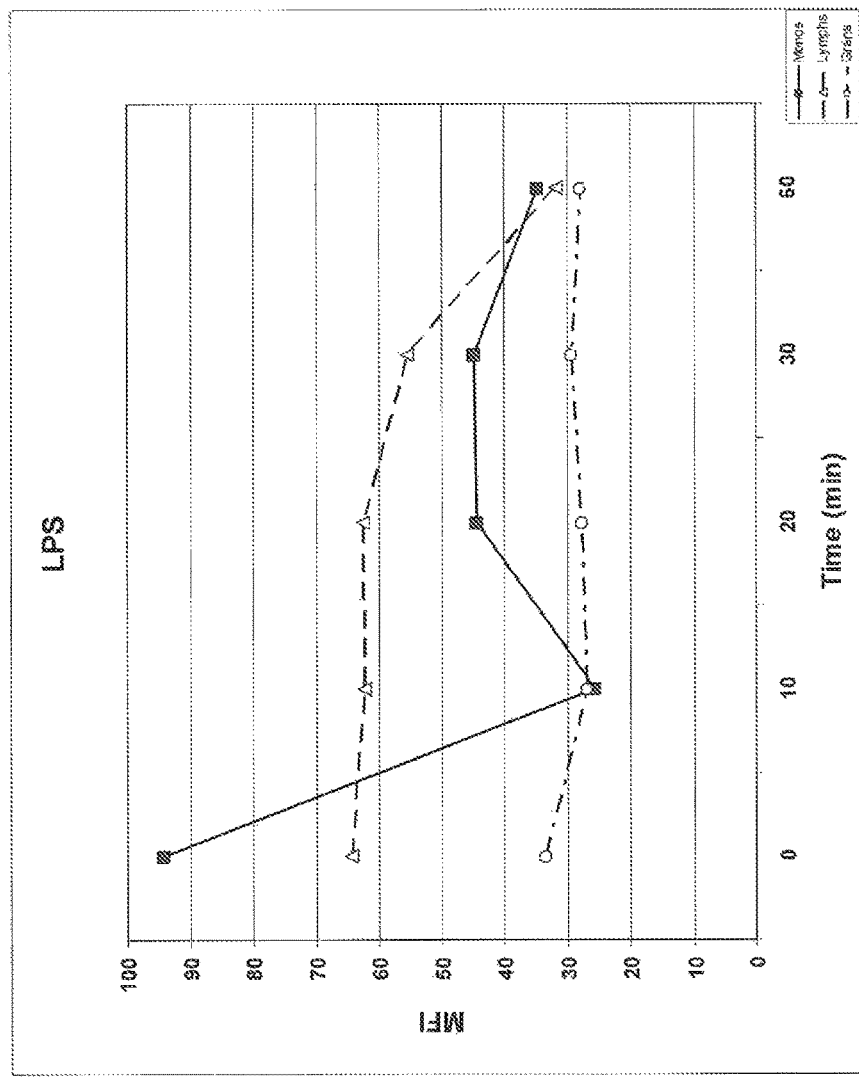
FIG. 2 shows the kinetics of LPS induced degradation of IκB in human peripheral blood monocytes (squares), lymphocytes (triangles), and granulocytes (circles).
Figure 3:
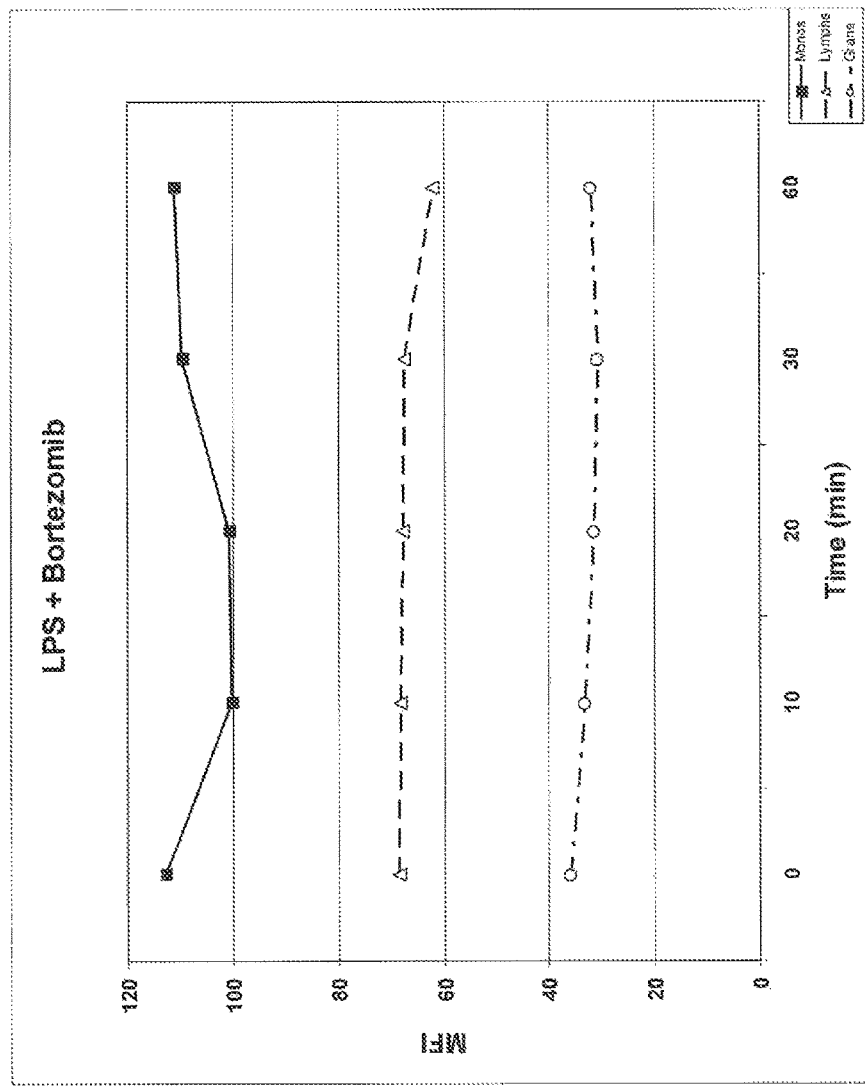
FIG. 3 shows inhibition of LPS induced degradation of IκB in peripheral blood monocytes (squares), lymphocytes (triangles), and granulocytes (circles) by the proteasome inhibitor Bortezomib.

In normal human donors, activation of the NF-κB pathway through a number of different cell surface receptors (including TLR4, the receptor tyrosine kinase activated by LPS) results in the phosphorylation of the IκBα protein by its upstream kinase, IKK. Phosphorylation of IκBα results in ubiquination and degradation of IκB by the proteasome complex and release of NF-κB proteins for subsequent nuclear localization. FIG. 2 shows the kinetics of LPS induced degradation of IκB in human peripheral blood monocytes (squares) and lymphocytes (triangles). No significant change in measured IκB levels was observed for granulocytes (circles) throughout the 60 minutes time period after LPS treatment. FIG. 3 shows the inhibition of LPS induced degradation of IκB in peripheral blood monocytes (squares) and lymphocytes (open triangles) treated with the proteasome inhibitor Bortezomib. No significant change in measured IκB levels was observed for granulocytes (open circles) throughout the 60 minutes time period after treatment with LPS and/or Bortezomib.

In the presence of Bortezomib, monocytes exhibited approximately a 10% loss in measured IκB. The degradation of IκB occurred within 10 minutes of treatment with LPS. In comparison, samples treated with LPS alone exhibited a 60-70% loss in measured IκB within 10 minutes of treatment. No significant degradation of IκB was observed for granulocytes in sample treated only with LPS (FIG. 2) or in samples treated with both Bortezomib and LPS (FIG. 3). The kinetics of IκB loss was also found to be different in monocytes and lymphocytes. In both FIGS. 2 and 3, monocytes exhibited a rapid decrease (10 min) in IκB, while lymphocytes exhibited no significant degradation of IκB at the same time point.

Figure 4:
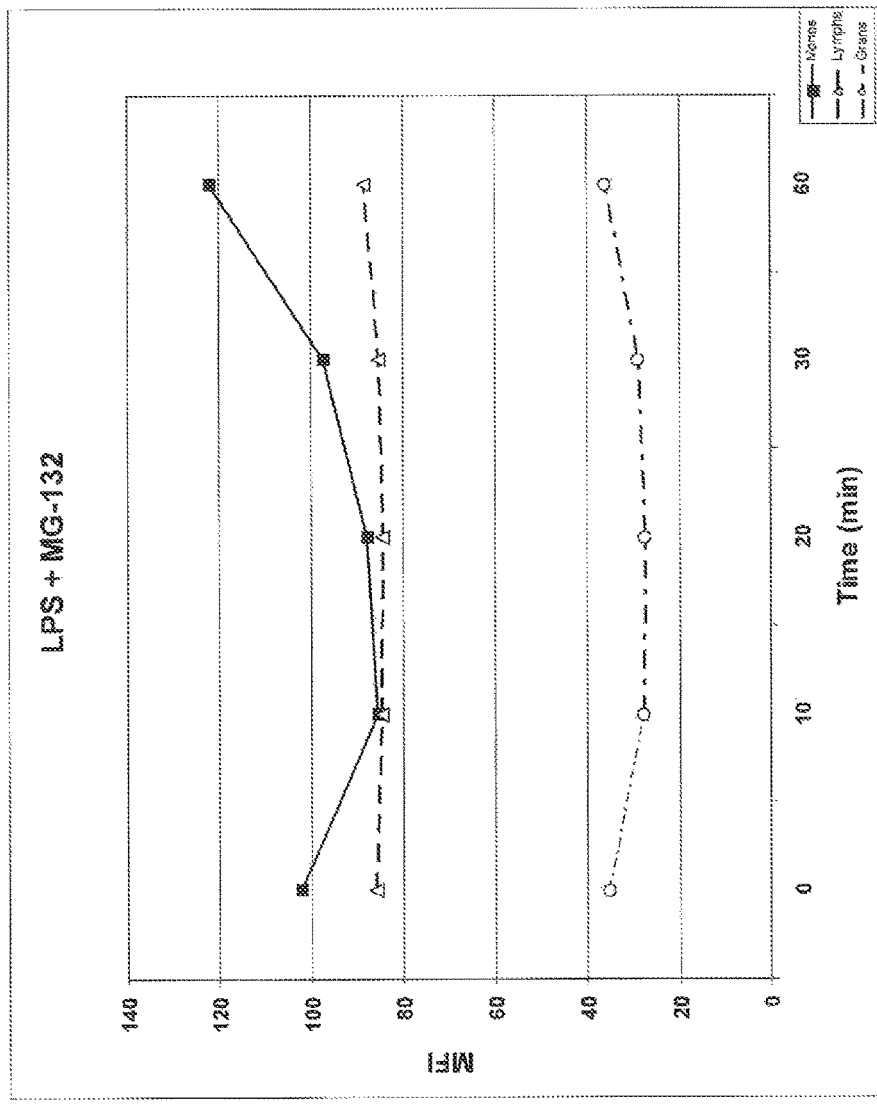
FIG. 4 shows inhibition of LPS induced degradation of IκB in peripheral blood monocytes (squares), lymphocytes (triangles), and granulocytes (circles) by the proteasome inhibitor MG-132.

FIG. 4 shows inhibition of LPS induced degradation of IκB in peripheral blood monocytes (squares), lymphocytes (triangles), and granulocytes (circles) by the proteasome inhibitor MG-132. No significant degradation of IκB was observed in LPS activated granulocytes or lymphocytes treated with MG-132. The kinetics of IκB degradation in LPS activated monocytes treated with MG-132 was similar to the LPS activated monocytes treated with Bortezomib.

This data demonstrates that IκB is a useful biomarker for monitoring proteasome activity in peripheral blood cells and validates the flow cytometry assay for the simultaneous analysis of proteasome activity in multiple subsets of cells in a biological sample. In both monocytes and lymphocytes, the degradation of IκB could be inhibited by treating the cells with a proteasome inhibitor.

Example 2

Monitoring of IκB and Phosphorylation of Signaling Pathways in Peripheral Blood WBCs Activated by LPS Phosphorylation of signaling pathways activated by LPS, including ERK, Akt (activated by PI3 Kinase), and the ribosomal S6 protein (a marker of protein synthesis) were also monitored together with the degradation of IκB. The effect of MG-132, a proteasome inhibitor, and GDC-0941, a PI3 kinase inhibitor, were studied in monocytes. Whole blood samples were treated, activated, and processed as described in Example 1. The degradation of IκB in cells pretreated with MG-132 or GDC-0941 was monitored by flow cytometry as described in Example 1. The IκB degradation agonist used in this example was LPS. Whole blood cells were stained with antibodies to IκB, phosphorylated Akt (P-Akt: P-Ser473), phosphorylated ERK (P-ERK; P-Thr202/P-Tyr204), and phosphorylated S6 (P-S6; P-Ser235/P-Ser236). Monocytes were identified by antibodies to CD14 and lymphocytes were identified by antibodies to CD3 and CD19.

Figure 5:
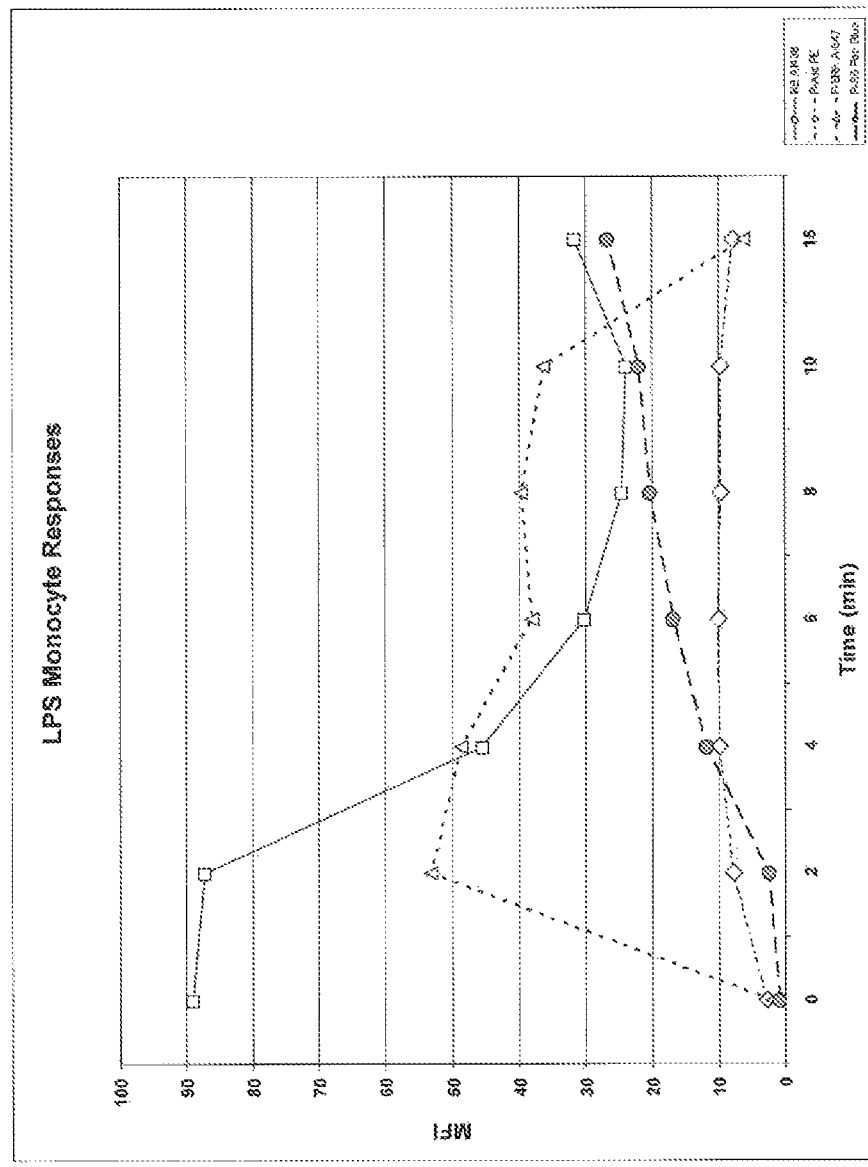
FIG. 5 shows the kinetics of IκB (squares) degradation and response of specific signaling pathways, ERK (triangles), Akt (diamonds), and S6 phosphorylation (circles), in peripheral blood monocytes activated by LPS.
Figure 6:
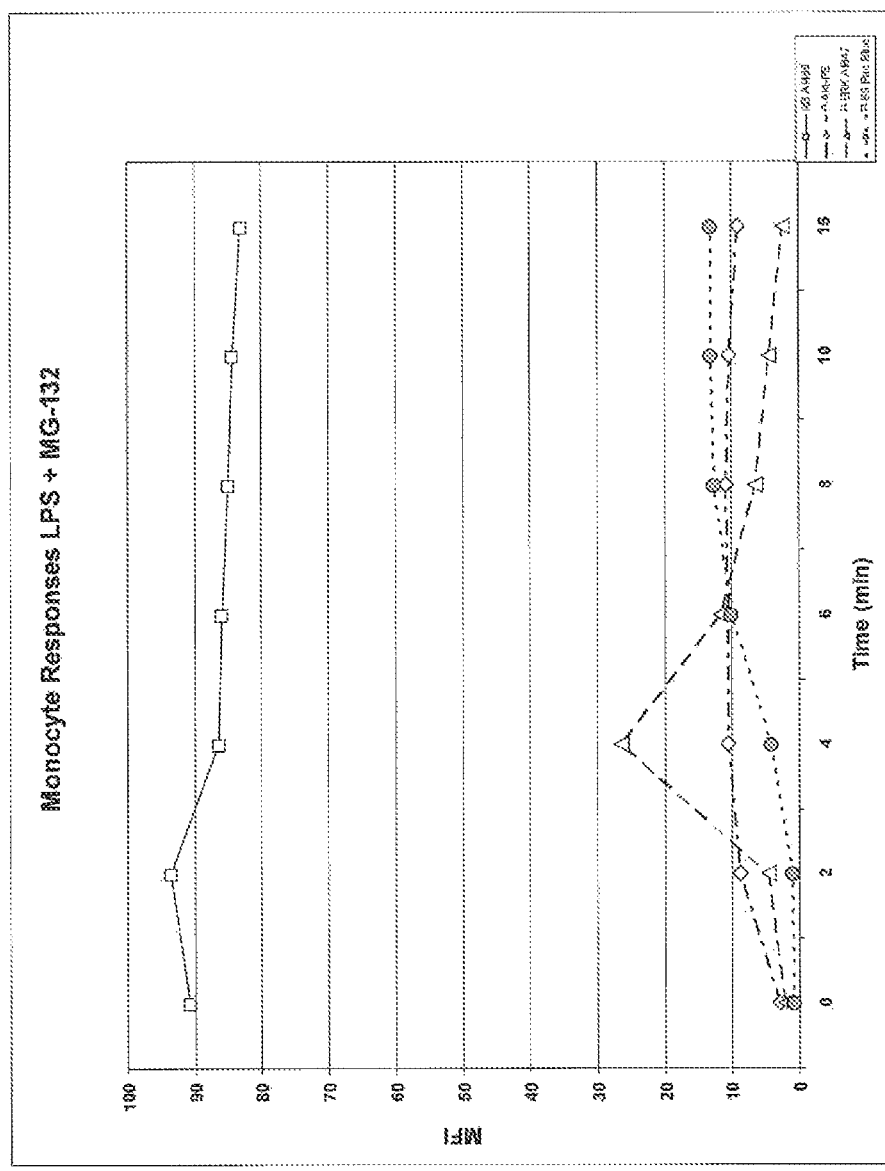
FIG. 6 shows the kinetics of IκB (squares) degradation and response of specific signaling pathways, ERK (triangles). Akt (diamonds), and S6 phosphorylation (circles), in LPS activated peripheral blood monocytes from whole blood pretreated with the proteasome inhibitor MG-132.
Figure 7:
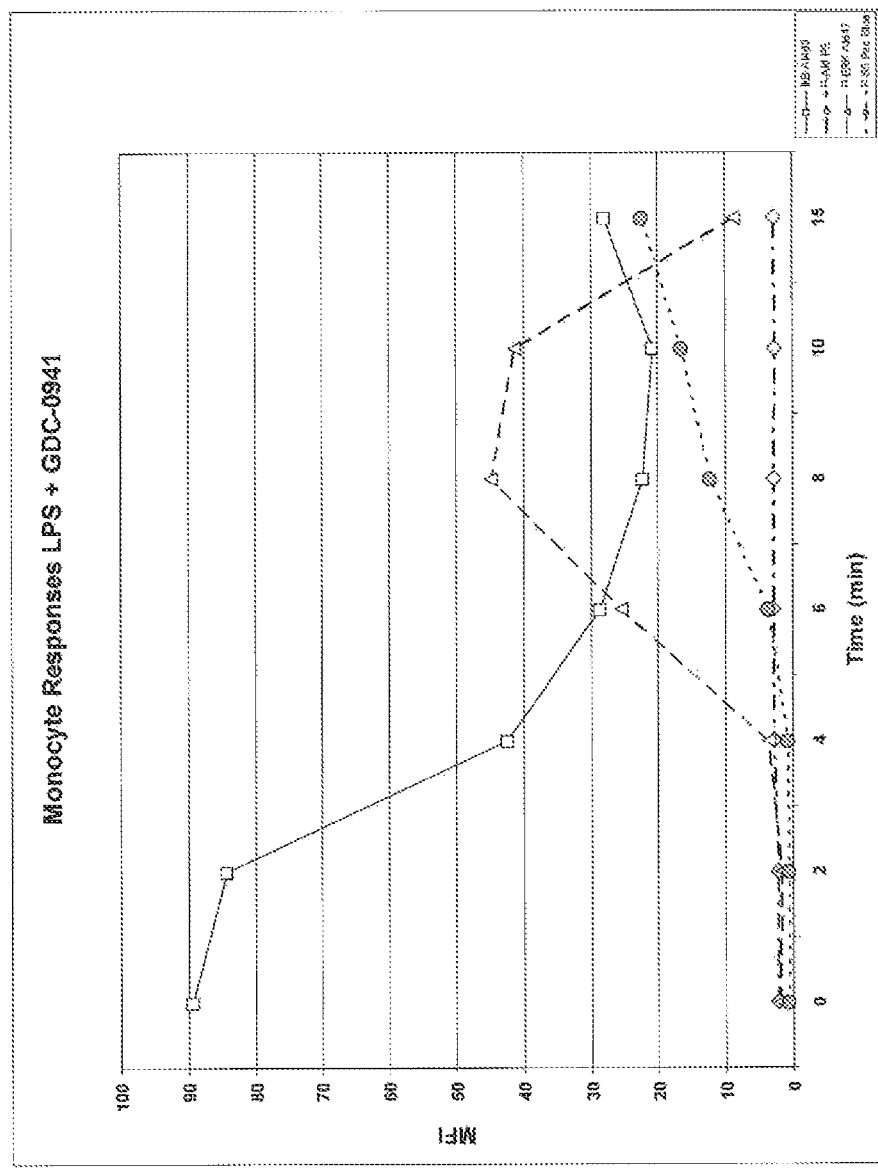
FIG. 7 shows the kinetics of IκB (squares) degradation and response of specific signaling pathways, ERK (triangles), Akt (diamonds), and S6 phosphorylation (circles), in LPS activated peripheral blood monocytes from whole blood pretreated with the PI3 kinase inhibitor GDC-0941.

The kinetics of IκB degradation (open squares) and phosphorylation of ERK 1/2 (triangles), Akt (diamonds), and ribosomal S6 protein (circles) after LPS induction is shown in FIG. 5. The kinetics of IκB (squares) degradation and activation response of ERK (triangles). Akt (diamonds), and S6 (circles) in LPS activated peripheral blood monocytes pretreated with MG-132 is shown in FIG. 6. MG-132 inhibited degradation of IκB and had no effect on Akt activation. The kinetics of IκB (squares) degradation and activation response of ERK (triangles), Akt (diamonds), and S6 (circles) in LPS activated peripheral blood monocytes pretreated with the proteasome inhibitor GDC-0941 is shown in FIG. 7. GDC-0941 inhibited Akt activation and had no effect on degradation of IκB.

Figure 16:
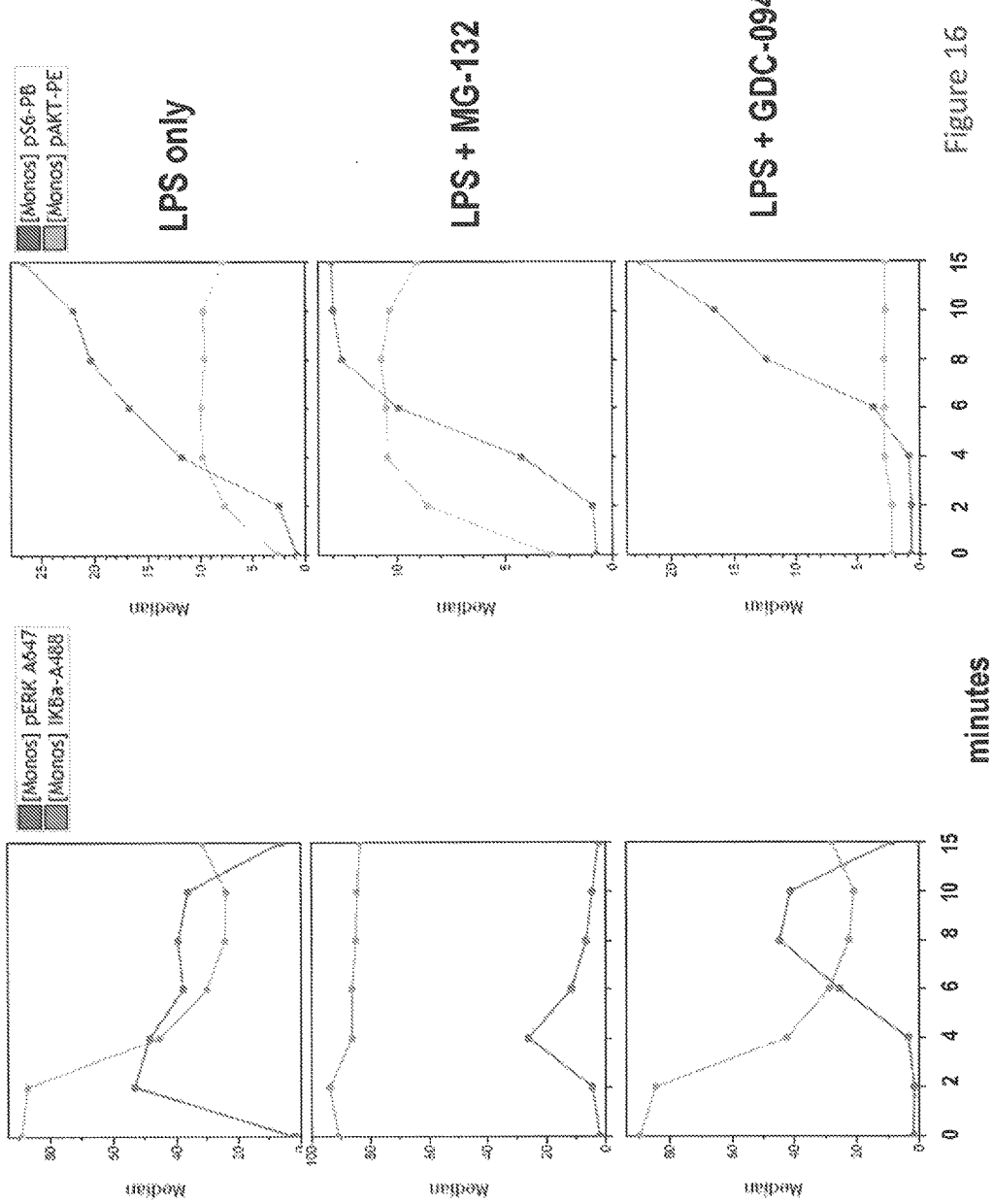
FIG. 16 shows the kinetics of monocyte signaling pathway responses to LPS activation (top row) in monocytes pretreated with a proteasome inhibitor, MG-132 (middle row), or a PI3 kinase inhibitor, GDC-0941 (bottom row). The left side panels show the kinetics of IκB degradation and ERK activation. The right side panels show the kinetics of Akt and S6 phosphorylation.

FIG. 16 shows the kinetics of monocyte signaling pathway responses to LPS activation with or without MG-132 or GDC-0941 pretreatment. The left side panels in FIG. 16 show the kinetics of IκB degradation and ERK activation. The right side panels show the kinetics of Akt and S6 phosphorylation.

Previous studies of LPS activation of peripheral blood monocytes have demonstrated two peaks of P-ERK phosphorylation, one peaking within 2-4 minutes ("early" P-ERK) of LPS activation, the second at about 10 minutes ("late" P-ERK). The "early" and "late" activation pathways are illustrated in FIG. 1. Pretreatment of whole blood samples with the PI3 kinase inhibitor GDC-0941 inhibited the "early" phosphorylation of ERK 1/2 in monocytes (FIG. 16, lower left panel), indicating that the early activation of ERK is through the PI3 kinase/Akt pathway. GDC-0941 inhibited Akt activation in monocytes (FIG. 16, lower right panel), serving as a positive control. GDC-0941 was found to have no impact on the degradation of IκB, and minimal impact on the activation of ribosomal S6 protein. In the presence of GDC-0941, the second ERK activation peak was found to be unchanged (FIG. 16, lower left panel), as was the magnitude of downstream phosphorylation of S6 ribosomal protein (onset of S6 phosphorylation was slightly delayed) (FIG. 16, lower right panel). Finally, GDC-0941 was found to have no impact on LPS induced destruction of IκB (FIG. 16, lower left panel), indicating the lack of a connection between IKK induced degradation of IκB and the PI3 kinase pathway. The middle panels of FIG. 16 show the effects of MG-132 on monocyte signaling pathway responses to LPS activation. Similar results were obtained with Bortezomib. MG-132 inhibited the degradation of IκB and inhibited the second (but not the first) ERK activation peak. Although the S6 protein is phosphorylated in the presence of MG-132, the MFI of the response was approximately 50% lower than in the sample treated with only LPS. These data are consistent with the concept that in peripheral blood monocytes, the activation of S6 protein is primarily via P-ERK. The middle right panel in FIG. 16 also shows that evidence that proteasome inhibition has no apparent effect on the PI3K-Akt pathway). Overall, these data are consistent with the model that the second phosphorylation of ERK (e.g., "late" P-ERK) is through the MAPK3 Tpl-2, which is sequestered in an inactive form on the p105 protein, and activated/phosphorylated subsequent to p105 degradation by the proteasome.

Example 3

Monitoring of IκB and Phosphorylation of Signaling Pathways in Peripheral Blood WBCs Activated by TNF-α

Phosphorylation of signaling pathways activated by TNF-α, including ERK, Akt, and the ribosomal S6 protein, was monitored together with the degradation of IκB in peripheral blood WBCs. Whole blood samples were treated, activated, and processed as described in Example 1 and the degradation of IκB in peripheral blood cells was monitored by flow cytometry as described in Example 1. The IκB degradation agonist used in this example was TNF-α. Whole blood cells were stained with antibodies to IκB, phosphorylated Akt (P-Akt: P-Ser473), phosphorylated ERK (P-ERK;

P-Thr202/P-Tyr204), and phosphorylated S6 (P-S6; P-Ser235/P-Ser236). Monocytes were identified by antibodies to CD14 and lymphocytes were identified by antibodies to CD3 and CD19. A portion of the whole blood samples were treated with proteasome inhibitor Bortezomib before TNF-α activation as described in Example 1.

Figure 8:
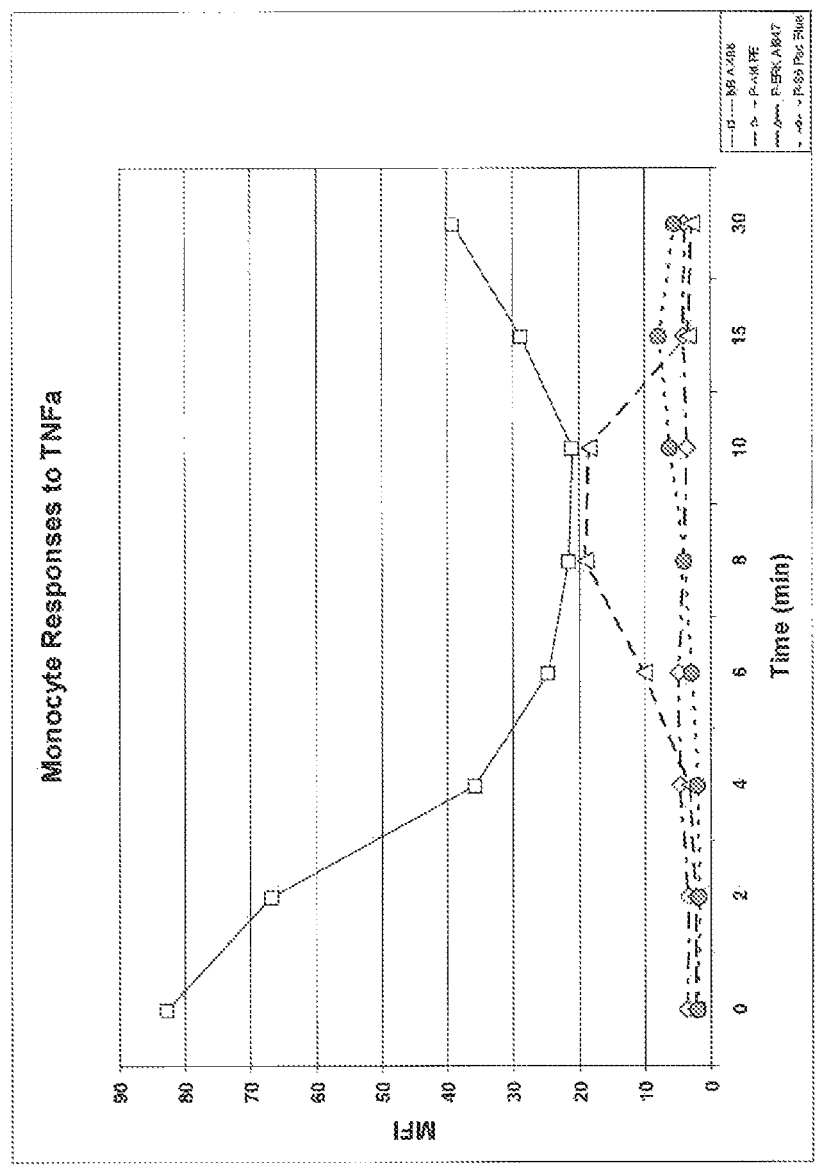
FIG. 8 shows the kinetics of IκB (squares) degradation and response of specific signaling pathways, ERK (triangles). Akt (diamonds), and S6 phosphorylation (circles), in peripheral blood monocytes activated by TNFα.
Figure 9:
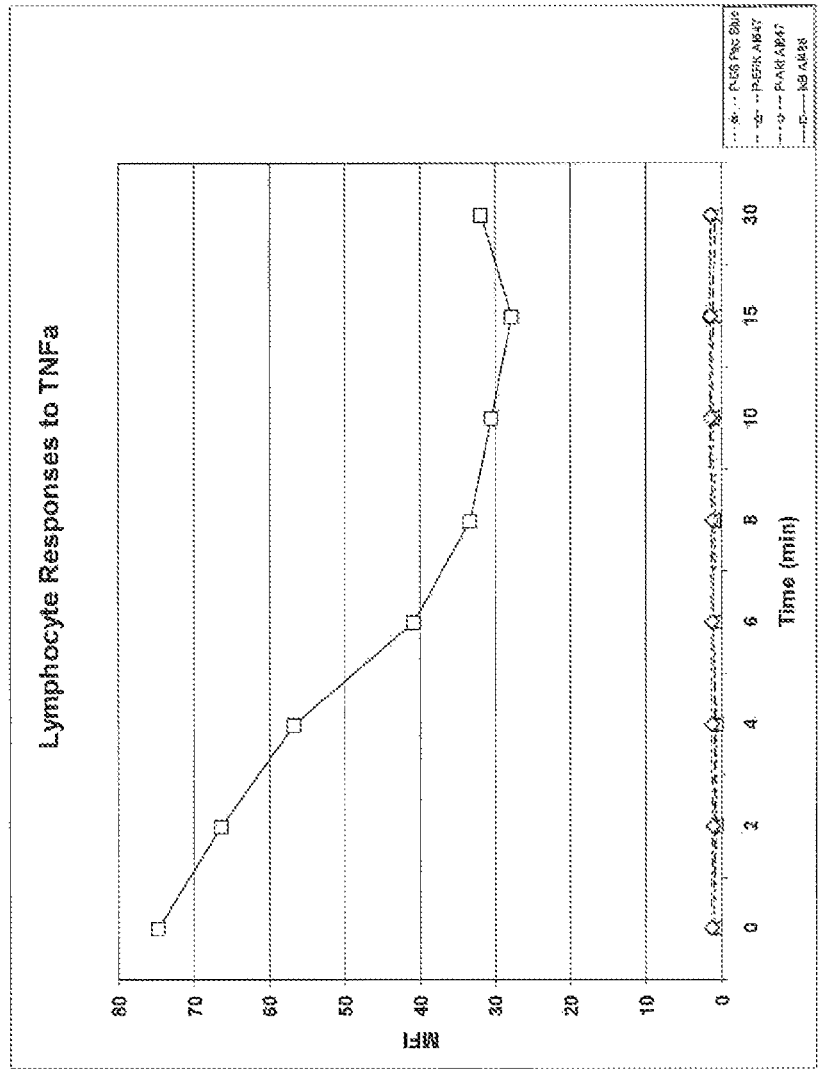
FIG. 9 shows the kinetics of IκB (squares) degradation and response of specific signaling pathways, ERK (triangles), Akt (diamonds), and S6 phosphorylation (circles), in peripheral blood lymphocytes activated by TNFα.

FIGS. 8 and 9 show the kinetics of IκB (squares) degradation and activation response of specific signaling pathways, ERK (triangles), Akt (diamonds), and S6 (circles), in peripheral blood monocytes and lymphocytes, respectively, activated by TNFα. TNFα activation induced degradation of IκB in both monocytes and lymphocytes. ERK was activated in monocytes but not lymphocytes. Neither Akt nor S6 was activated by TNFα in monocytes or lymphocytes.

Figure 17:
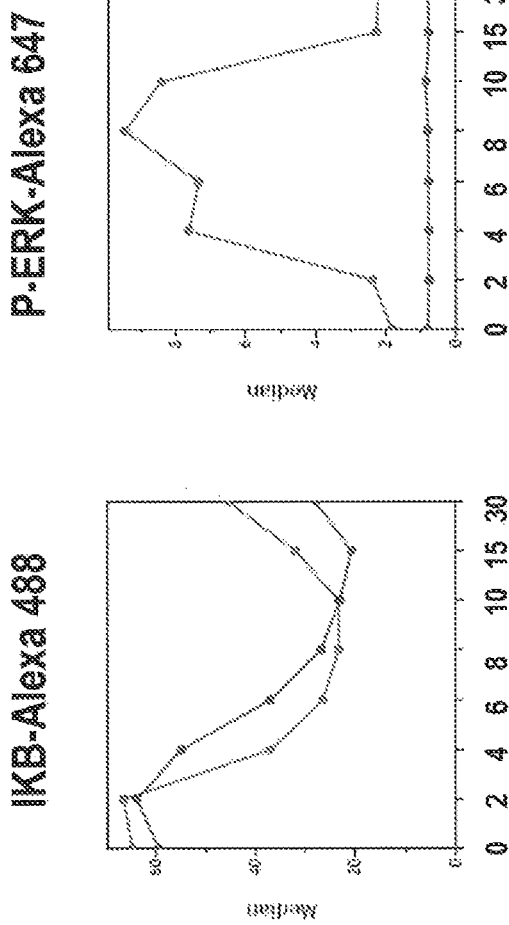
FIG. 17 shows a comparison of IκB degradation (left panel) and ERK activation (right panel) between peripheral blood monocytes and lymphocytes in whole blood treated with TNF-α.

FIG. 17 shows a comparison of IκB degradation (left panel) and ERK activation (right panel) between peripheral blood monocytes and lymphocytes in whole blood treated with TNF-α. The TNF-α caused degradation of IκB in peripheral blood monocytes with a peak loss at 10 minutes after stimulation. This response was found to be similar to that observed in monocytes following LPS stimulation. The TNF-α caused degradation of IκB in peripheral blood lymphocytes with a peak loss at 15 minutes after stimulation (FIG. 17, left panel). TNF-α activation resulted in an activation pattern for ERK in monocytes that was similar to the ERK activation pattern observed in monocytes following LPS stimulation, with no apparent response in lymphocytes. Detailed analysis of the lymphocyte response to TNF-α activation revealed a subpopulation of lymphocytes degrade IκB and also activate ERK or Akt (data not shown).

Figure 10:
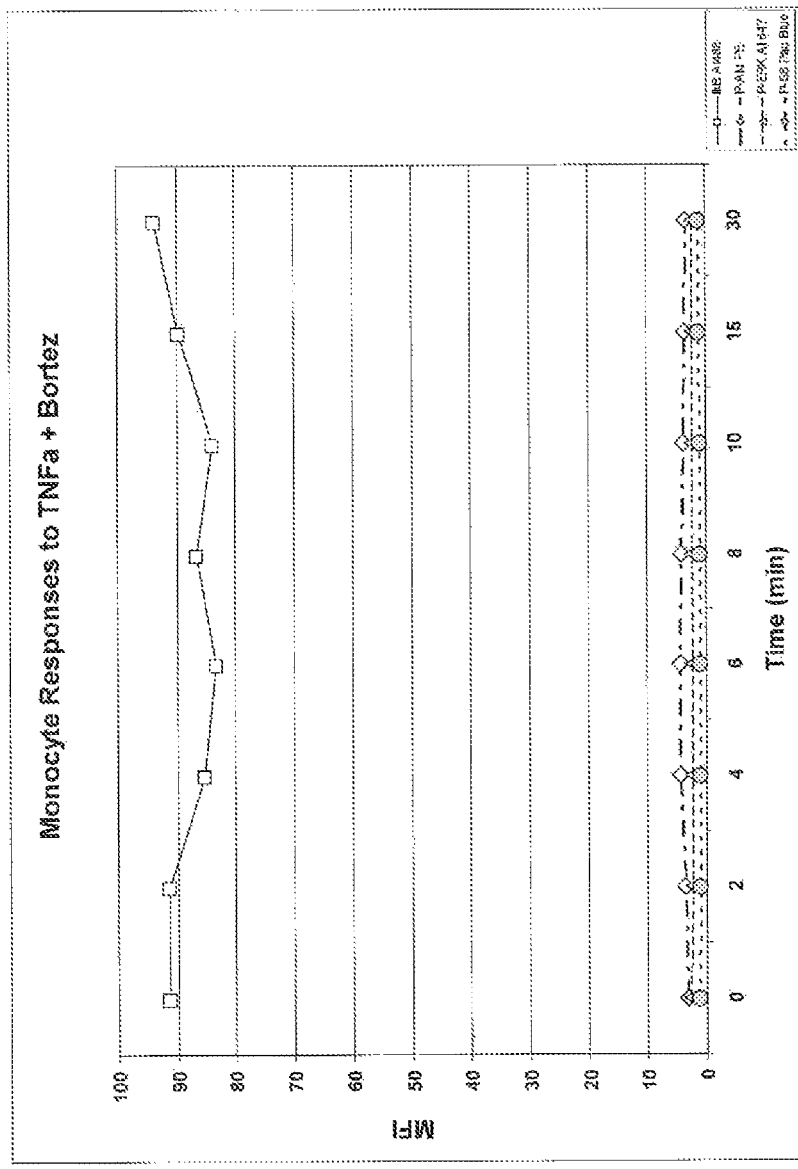
FIG. 10 shows the kinetics of IκB (squares) degradation and response of specific signaling pathways, ERK (triangles). Akt (diamonds), and S6 phosphorylation (circles), in TNFα activated peripheral blood monocytes from whole blood pretreated with the proteasome inhibitor Bortezomib.

The kinetics of IκB (squares) degradation and response of specific signaling pathways, ERK (triangles), Akt (diamonds), and S6 (circles), in TNFα activated peripheral blood monocytes from whole blood pretreated with the proteasome inhibitor Bortezomib is shown in FIG. 10. Pretreatment with Bortezomib completely inhibited the degradation of IκB and activation of ERK. Similar results were obtained with the proteasome inhibitor MG-132 (data not shown).

Example 4

Monitoring of IκB and Phosphorylation of Signaling Pathways in Peripheral Blood WBCs Activated by CD40L Phosphorylation of signaling pathways activated by CD40L, including ERK, Akt, and the ribosomal S6 protein, was monitored together with the degradation of IκB in peripheral blood WBCs. Whole blood samples were treated, activated, and processed as described in Example 1 Degradation of IκB in peripheral blood cells was monitored as described in Example 1 by flow cytometry. The IκB degradation agonist used in this example was CD40L. Whole blood cells were stained with antibodies to IκB, phosphorylated Akt (P-Akt; P-Ser473), phosphorylated ERK (P-ERK; P-Thr202/P-Tyr204), and phosphorylated S6 (P-S6; P-Ser235/P-Ser236). Monocytes were identified by antibodies to CD4 and lymphocytes were identified by antibodies to CD3 and CD19.

Figure 12:
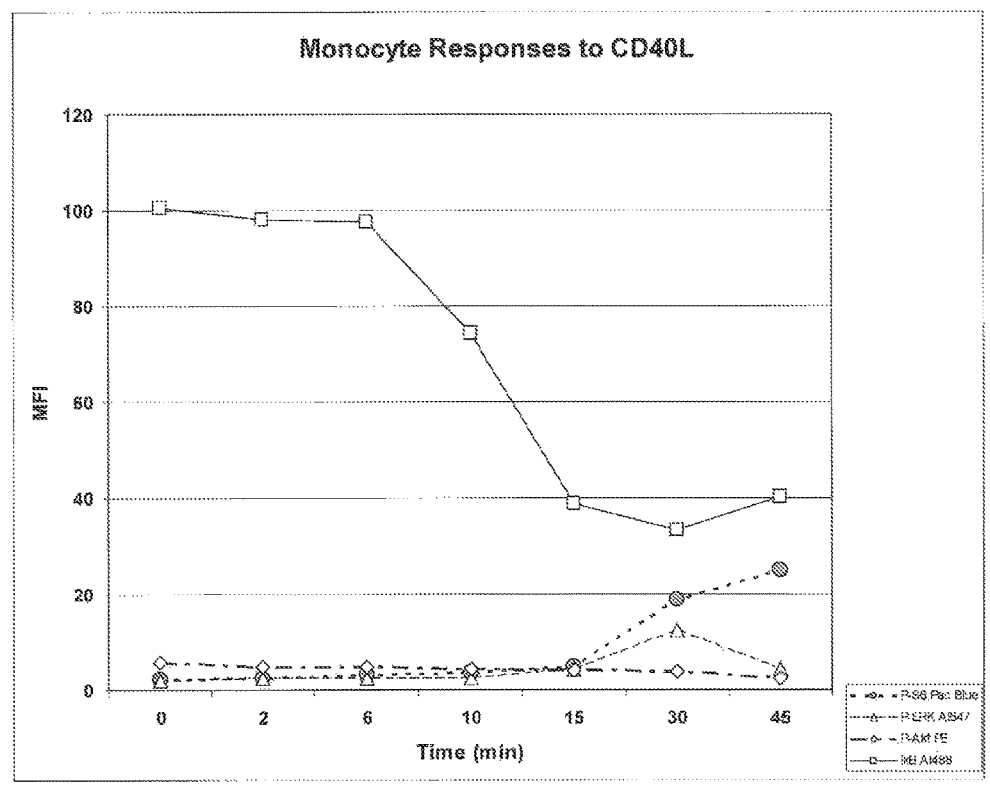
FIG. 12 shows the kinetics of IκB (squares) degradation and response of specific signaling pathways, ERK (triangles), Akt (diamonds), and S6 phosphorylation (circles), in peripheral blood monocytes activated by CD40L.
Figure 13:
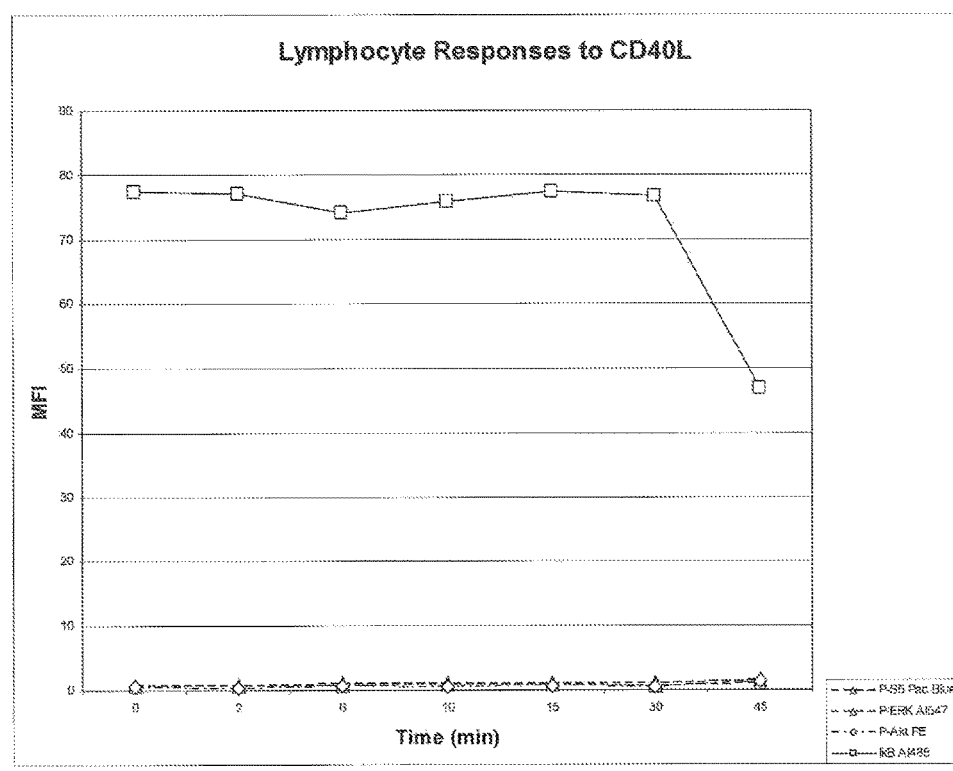
FIG. 13 shows the kinetics of IκB (squares) degradation and activation response of specific signaling pathways, ERK (triangles), Akt (diamonds), and S6 phosphorylation (circles), in peripheral blood lymphocytes activated by CD40L.

FIGS. 12 and 13 show the kinetics of IκB (squares) degradation and activation response of specific signaling pathways, ERK (triangles), Akt (diamonds), and S6 (circles), in peripheral blood monocytes and lymphocytes, respectively, activated by CD40L. In monocytes the level of IκB, decreased approximately 60% between 6 and 15 minutes post treatment with CD40L (FIG. 12). In contrast, the level of IκB remained stable in lymphocytes 30 minutes post treatment but then decreased by approximately 40% between 40 and 45 minutes post treatment (FIG. 13). Akt was not activated by CD40L in monocytes or lymphocytes. CD40L stimulated a low level of ERK activation beginning 15 minutes post treatment (FIG. 12). The activation of ERK coincided with a stabilization in the level of IκB. Neither ERK nor S6 were activated in the lymphocytes (FIG. 13).

Example 5

Monitoring of IκB and Phosphorylation of Signaling Pathways in Peripheral Blood WBCs Activated by PMA Phosphorylation of signaling pathways activated by PMA, including ERK and Akt, was monitored together with the degradation of IκB in peripheral blood WBCs. Whole blood samples were treated, activated, and processed as described in Example 1. Degradation of IκB in peripheral bloods cells was monitored as described in Example by flow cytometry. The IκB degradation agonist used in this example was PMA. Whole blood cells were stained with antibodies to IκB, phosphorylated Akt (P-Akt; P-Ser473), phosphorylated ERK (P-ERK; P-Thr202/P-Tyr204), and phosphorylated S6 (P-S6; P-Ser235/P-Ser236). Monocytes were identified by antibodies to CD14 and lymphocytes were identified by antibodies to CD3 and CD19.

Figure 14:
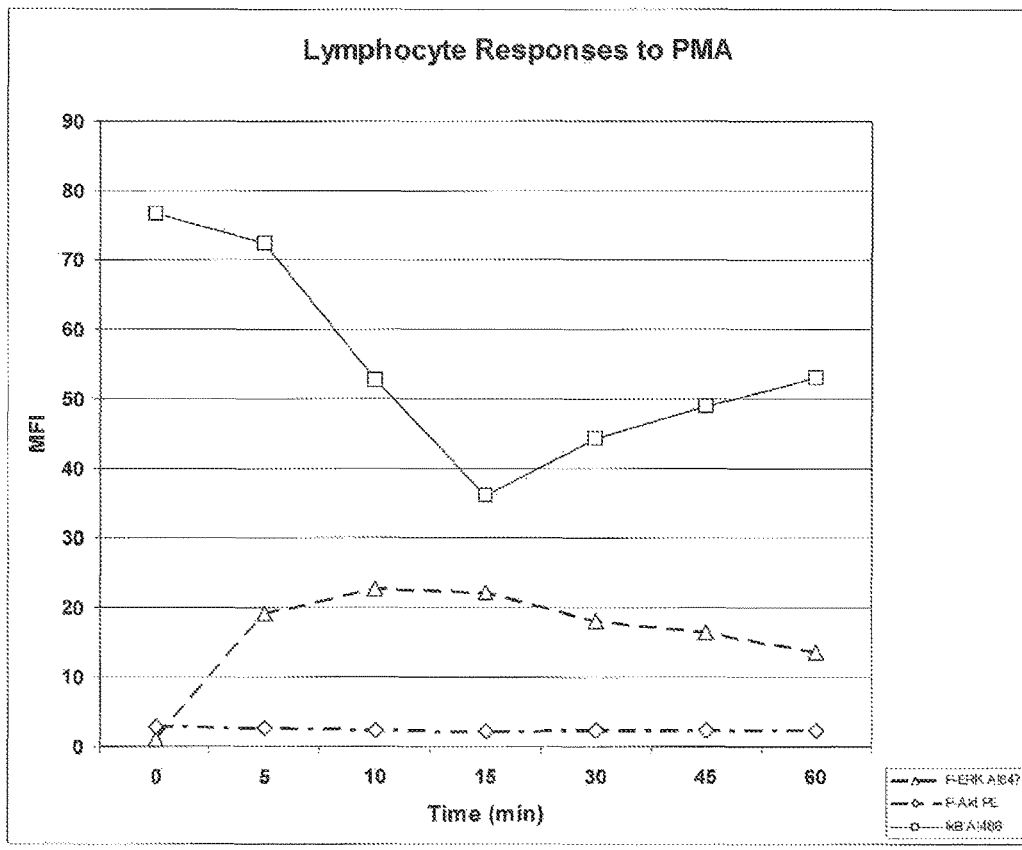
FIG. 14 shows the kinetics of IκB (squares) degradation and response of specific signaling pathways, ERK (triangles) and Akt (diamonds), in peripheral blood lymphocytes activated by PMA.

The kinetics of IκB (squares) degradation and activation response of specific signaling pathways, ERK (triangles) and Akt (diamonds), in peripheral blood lymphocytes activated by PMA is shown in FIG. 14. PMA stimulated the degradation of IκB and activation of ERK which was sustained at a relatively elevated level from 5 minutes to 60 minutes post treatment. Akt was not activated in the lymphocytes by PMA.

Figure 15:
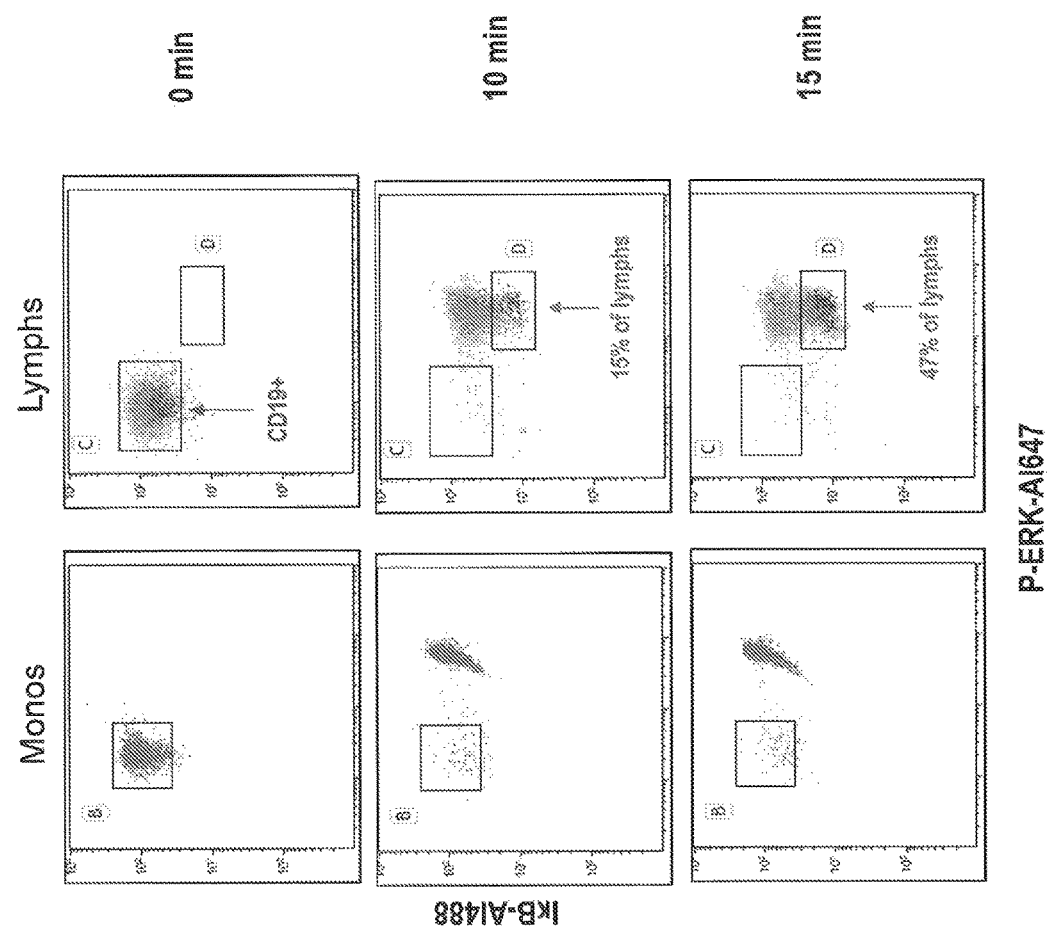
FIG. 15 provides flow cytometric dot plots showing IκB degradation (y-axis) and ERK activation (x-axis) in monocytes (left column) and lymphocytes (right column) at 0 min (top row), 10 min (middle row), and 15 min (bottom row) post activation with PMA.

FIG. 15 shows flow cytometric dot plots showing IκB degradation (y-axis) and ERK activation (x-axis) in monocytes (left column) and lymphocytes (right column) at 0 min (top row), 10 min (middle row), and 15 min (bottom row) post activation with PMA. Box B shows the monocyte population at time 0. Activation of the monocytes with PMA resulted in the activation of ERK with no degradation of IκB (FIG. 15, left column). In contrast, PMA activation of the lymphocytes resulted in both the degradation of IκB and the activation of ERK in approximately 50% of the lymphocytes over the 15 min time course. Box C shows the lymphocyte population (CD19+) at time 0. The cells in box D are lymphocytes in which PMA activation resulted in both the degradation of IκB and the activation of ERK.

Table 1 below summarizes the results of the IκB degradation agonists studied in Examples 1-5 including the signaling pathways activated and the target cell population(s) of the agonist.

TABLE 1

| Agonist | Pathways Activated | Target Cell Population |
|---------|--------------------|------------------------|
| LPS | Tpl-2 > ERK/MAP kinase<br>SAP/JNK MAP kinase<br>P-p 38 MAP kinase<br>PI3 kinase > Akt<br>IκB > NFκB | Monocytes |

TABLE 1-continued

| Agonist | Pathways Activated | Target Cell Population |
|---|---|---|
| | IκB > NFκB<br>ERK MAP kinase (Tpl-2)<br>PI3 kinase > Akt | Lymphocytes<br>(subpopulation) |
| | P-p38 MAP kinase | Granulocytes |
| TNFα | IκB > NFκB<br>Tpl-2 > ERK/MAP kinase<br>PI3 kinase > Akt | Monocytes |
| | IκB > NFκB<br>ERK/MAP kinase (Tpl-2)<br>PI3 kinase > Akt | Lymphocytes<br>(subpopulation) |
| | P-p38 MAP kinase | Granulocytes |
| CD40L | IκB > NFκB<br>Tpl-2 > ERK/MAP kinase<br>P38 MAP kinase | Monocytes |
| | IκB > NFκB (Tpl-2)<br>Tpl-2 > ERK/MAP kinase<br>PI3 kinase > Akt | Lymphocytes<br>(subpopulation) |
| PMA | P-ERK/MAP kinase (Ras > Raf)<br>(IκB is not degraded) | Monocytes |
| | IκB > NFκB (PKC?)<br>P-ERK/MAP kinase (Ras > Raf)<br>P-S6 (P-ERK) | Lymphocytes<br>(subpopulations) |
| | P-ERK/MAP kinase | Granulocytes |

Example 6

Monitoring of IκB and Phosphorylation of Signaling Pathways in Peripheral Blood WBCs Activated by Anti-CD28 and Anti-CD28/CD3

Phosphorylation of signaling pathways activated by anti-CD28, including ERK, was monitored together with the degradation of IκB in peripheral blood WBCs. For T-cell activation, 700 μL of heparinized whole blood was aliquotted into 4 separate 4 mL tubes. Either 10 μM Bortezomib or an equivalent volume of vehicle (100% EtOH) was added to each tube (2 per condition), and they were incubated for 2 hours in a 37° C. water bath. Following the 2-hour incubation, either 2.5 μg/mL anti-CD28 (CD28.2; Becton Dickinson) or 0.25 μg/mL anti-CD3 (OKT3: eBioscience)+2.5 μg/mL anti-CD28 were added to 1 tube for each condition, and they were then incubated for 15 minutes at room temperature. During the incubation period, individual 4 mL tubes for each sample+stimulation time point were labeled and 100 μL of the samples were aliquotted into their respective tubes (i.e., Control, 2.5, 5, 10, 15, or 20 min). After 15 minutes, goat-α-mouse F(ab')2 crosslinker (Jackson Immunoresearch) was added to the 20-minute time points, they were gently vortexed, and then immediately added to the 37° C. water bath. This process was repeated and each subsequent sample was timed in reverse so that all time points for each condition completed their stimulation at the same time, with each condition staggered by 10 seconds. The control samples were identical to the 2.5 minute time points, except that they did not receive the addition of crosslinker. Upon completion of stimulation, the samples were fixed and permeabilized using a PerFix-P kit (Beckman Coulter), blocked with normal mouse serum (Sigma) to prevent non-specific antibody binding to the crosslinker, and then stained for 30 minutes in the dark at room temperature, using the following antibodies: IκBα-AF488, pERK-AF647 (Cell Signaling Technology), CD4-KrO, and CD8-PB (Beckman Coulter). Finally, the samples were read on a GALLIOS™ flow cytometer (Beckman Coulter), and the data were analyzed using KALUZA™ software (Beckman Coulter).

Figure 20:
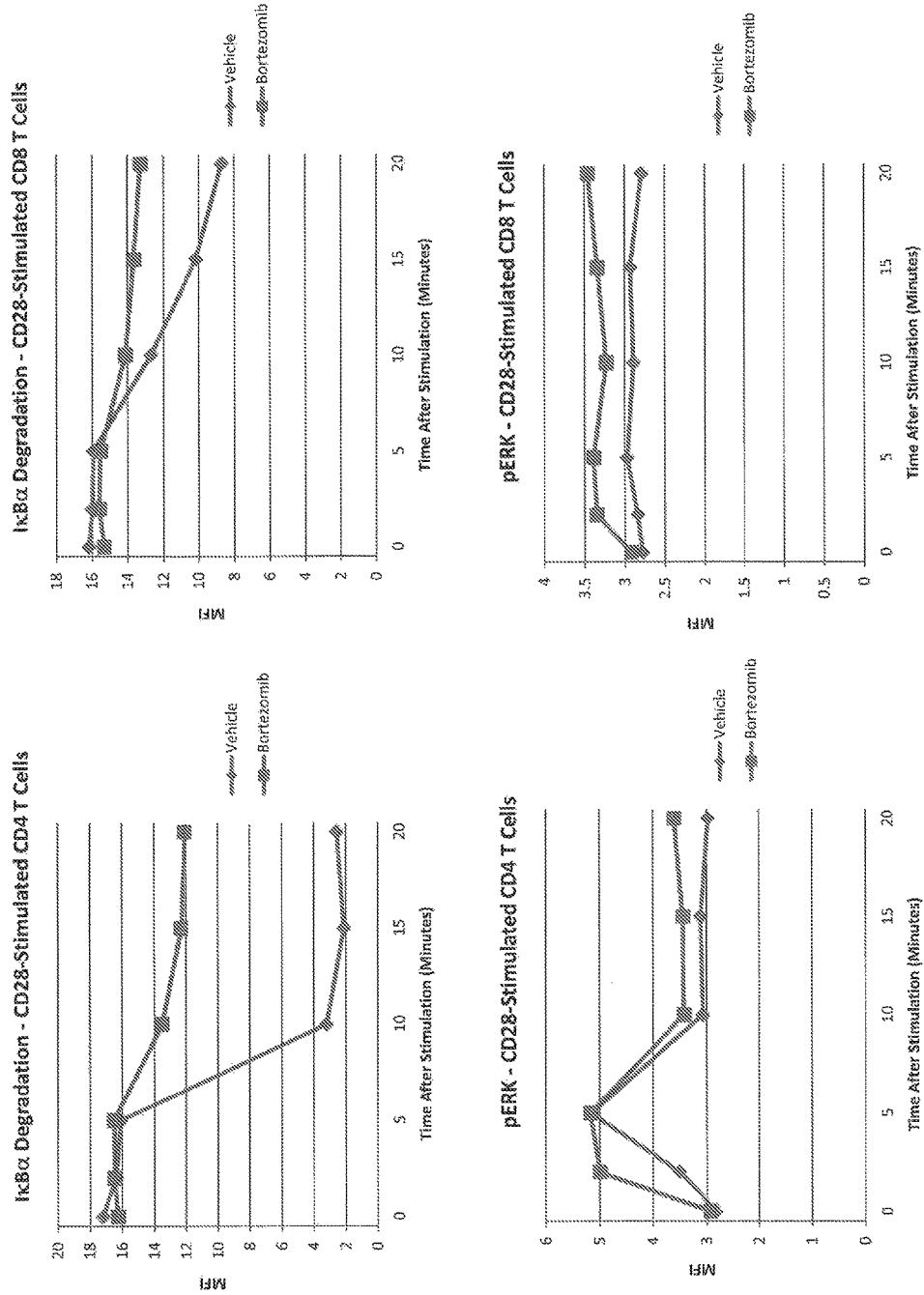
FIG. 20 shows the effect of anti-CD28 as IκB degradation agonist in CD4 and CD8 T cells on IκB degradation and ERK activation in the presence (squares) and absence (diamonds) of Bortezomib.
Figure 21:
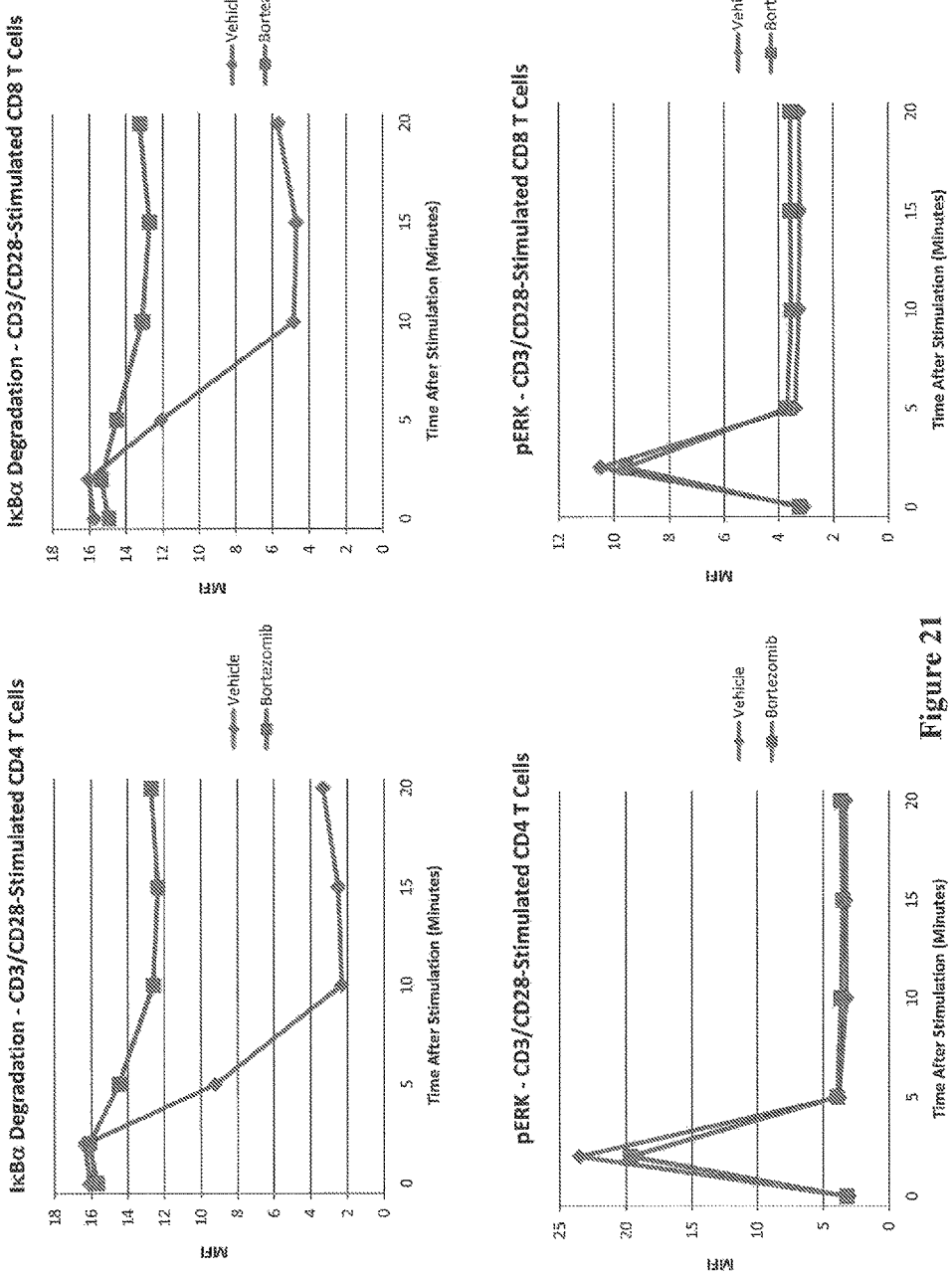
FIG. 21 shows the effect of anti-CD3/CD28 as IκB degradation agonist in CD4 and CD8 T cells on IκB degradation and ERK activation in the presence (squares) and absence (diamonds) of Bortezomib.

FIG. 20 shows the effect of anti-CD28 as IκB degradation agonist in CD4 and CD8 T cells on IκB degradation and ERK activation in the presence (squares) and absence (diamonds) of Bortezomib. FIG. 21 shows the effect of anti-CD3/CD28 as IκB degradation agonist in CD4 and CD8 T cells on IκB degradation and ERK activation in the presence (squares) and absence (diamonds) of Bortezomib.

Example 7

Flow Cytometry Assay for Detecting Inhibition of Proteasome Activity

This example demonstrates an exemplary embodiment of a flow cytometry assay for detecting the inhibition of proteasome activity by a proteasome effector. Two different whole blood samples were obtained and the samples treated, activated, and processed according to the flow cyotmetry assay described in Example 1. Aliquots of the first sample were treated with MG-132, a proteasome inhibitor, or U0126, a MEK inhibitor, prior to contacting the sample with the IκB degradation agonist. The second sample was subjected to similar treatment except UO 126 was no tested. The degradation of IκB in monocytes was analyzed by flow cytometry as described in Example 1. The IκB degradation agonist used in this example was LPS. The whole blood cells were stained with antibodies to IκB and phosphorylated ERK (P-ERK; P-Thr202/P-Tyr204). Monocytes were identified by antibodies to CD14.

Figure 19:
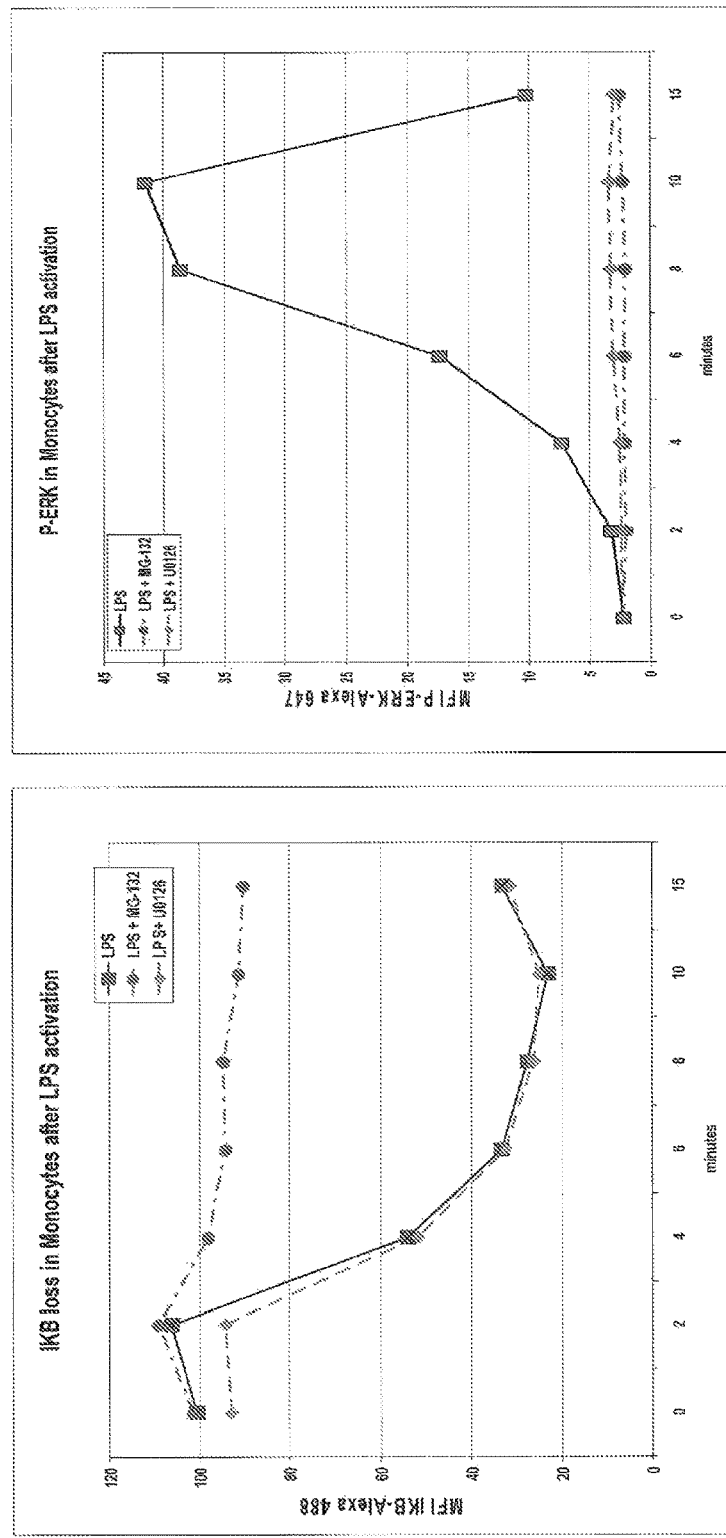
FIG. 19 shows IκB degradation (left panel) and ERK activation (right panel) in monocytes in whole blood after LPS stimulation (squares), in monocytes in whole blood pretreated with MG-132, a proteasome inhibitor (circles), prior to LPS stimulation, and in monocytes in whole blood pretreated with U0126, a MEK inhibitor (diamonds), prior to LPS stimulation.

A majority of the blood samples tested were found to have just one ERK peak, a late peak between 8-10 minutes as shown in FIG. 19. FIG. 19 shows IκB degradation (left panel) and ERK activation (right panel) in monocytes in whole blood after LPS stimulation (squares), monocytes in whole blood pretreated with MG-132 (circles) prior to LPS stimulation, and monocytes in whole blood pretreated with U0126 (diamonds) prior to LPS stimulation. FIG. 19 shows the single late ERK peak that was often observed. U0126 inhibits MEK upstream of ERK, so ERK is inhibited as shown by the right panel in FIG. 19.

Figure 11:
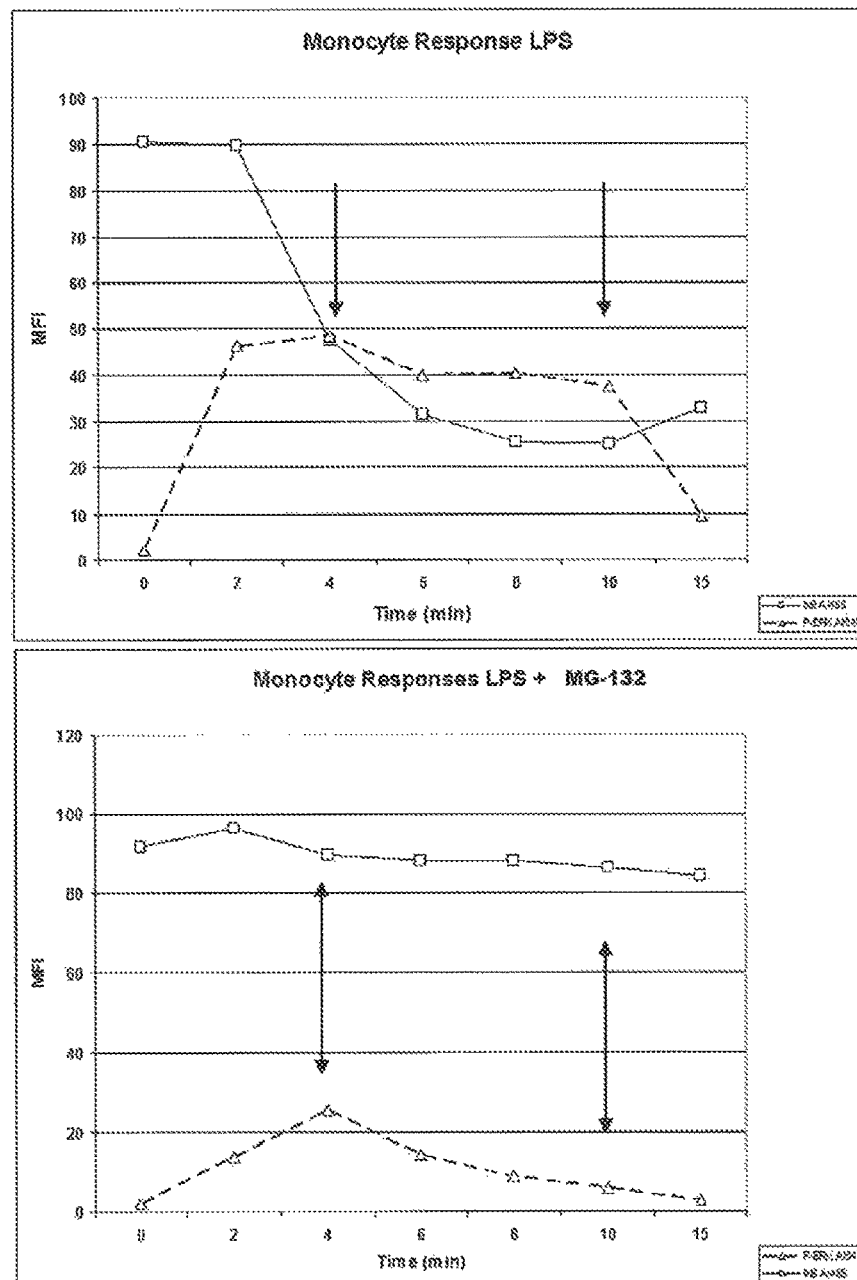
FIG. 11 shows the results of an exemplary proteasome assay according to an embodiment of the disclosure to detect inhibition of proteasome activity. The top panel shows the degradation of IκB (squares) and activation of ERK (triangles) in LPS activated peripheral blood monocytes. The bottom panel shows the degradation of IκB (squares) and activation of ERK (triangles) in LPS activated peripheral blood monocytes from whole blood pretreated with the proteasome inhibitor MG-132.

While the late P-ERK peak was found to be present in all samples, the presence and magnitude of the early P-ERK peak (typically between 2-4 minutes) can be variable. FIG. 11 shows an example of the sample with two ERK peaks. The top panel of FIG. 11 shows the degradation of IκB (squares) and activation of ERK (triangles) in LPS activated peripheral blood monocytes. The bottom panel shows the degradation of IκB (squares) and activation of ERK (triangles) in LPS activated peripheral blood monocytes from whole blood pretreated with MG-132. LPS stimulation for 8-10 min resulted in maximal level of IκB degradation, that is inhibited by proteasome inhibitors.

The data in FIGS. 11 and 19 also suggest that sensitivity and/or specificity of the proteasome assay can be further increased by simultaneously measuring of IκB degradation and ERK activation at a "late" time point (8-10 minutes).

Example 8

Flow Cytometry Assay for Monitoring and Evaluating Treatment of Multiple Myeloma with Proteasome Inhibitor Because proteasome inhibitors are commonly used to treat Multiple Myeloma (MM), this disorder was selected to check if there are significant differences in magnitude and/or kinetics of IκBα degradation in monocytes from normal blood and blood of MM patients that may prevent implementation of the assay of the disclosure.

Whole blood samples from eight Multiple Myeloma (MM) patients were obtained. For three of the MM patients (MM003-MM005), whole blood samples were tested with or without LPS activation (10 min stimulation at 37° C.) and the samples were processed and analyzed for IκB degradation and signaling pathway activation as described in Example 1. In these three MM patients, no inhibition of IκB degradation or ERK activation following LPS stimulation was observed (data not shown). This result was not surprising considering the short half-life of Bortezomib in circulation.

Figure 18:
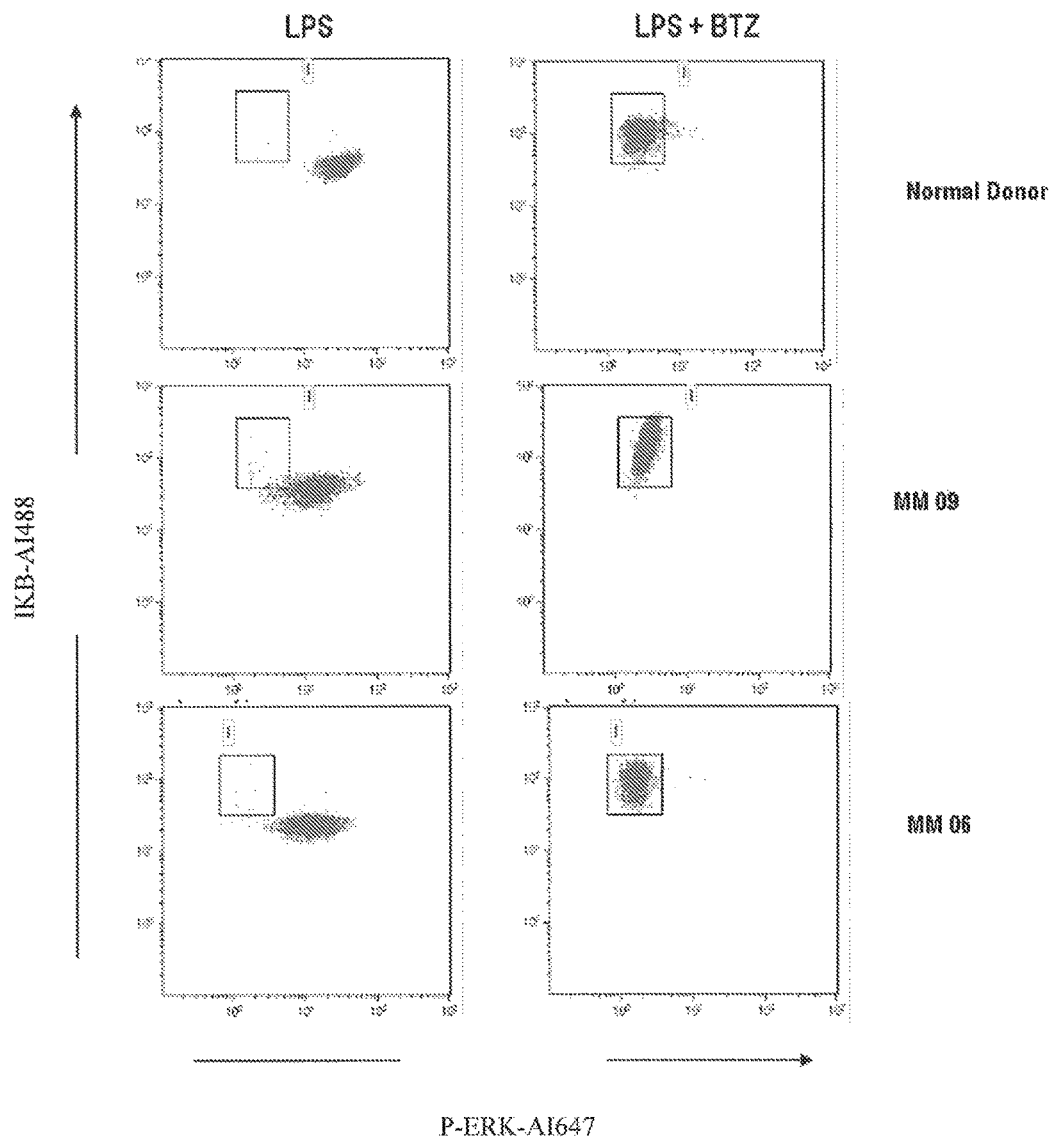
FIG. 18 shows that antibody staining of peripheral monocytes in whole blood samples from MM patients (middle row and bottom row) compared to normal donor (top row) with (right column) or without (left column) Bortezomib treatment.

Blood samples from the 5 remaining MM patients samples were pretreated with Bortezomib or RP-171 (Carfilzomib, a covalent proteasome inhibitor) and then tested and analyzed with or without LPS activation (10 min LPS at 37 37° C.) for IκB degradation and signaling pathway activation as described in Example 1. Representative results for two of the five MM patients compared to a normal donor are shown in FIG. 18. The MFI of P-ERK expression of MM monocytes is slightly lower than seen in normal donors. Six MM samples tested exhibited similar monocyte responses to LPS stimulation (60-70% loss of IκB) and in the two MM samples, the percent decrease of IκB MFI was lower than seen in normal monocytes (48% loss). All of the MM patients tested were receiving Bortezomib therapy. However, no proteasome inhibition was detected because the blood draw was performed a week after the treatment. Due to a very short half-life of Bortezomib in circulation it was already eliminated at the time of blood draw.

The results of this experiment demonstrate that the IκB degradation and ERK activation was not significantly altered in monocytes of MM patients, and the flow cytometry proteasome assay of current invention can be used in patient population currently targeted by proteasome inhibitors. Circulating MM cells were not detected in these samples (MM cells are seen in peripheral circulation only in later stages of the disease), and the LPS response of all eight samples was not significantly different from that seen in normal donors, measuring decrease in IκB and phosphorylation of ERK.

The results of this experiment further suggest that monitoring proteasome function in peripheral blood samples, in particular peripheral blood monocytes, from MM patients immediately before, and at timed intervals after Bortezomib therapy, according to the flow cytometry assay described herein can be used to determine the impact of dosing/time on proteasome function in vivo to determine if the serum levels of the drug are sufficient to achieve proteasome inhibition. The exemplified proteasome inhibition assay therefore is useful for pharmacodynamic assessment of proteasome inhibitors in patients.

While certain embodiments of the invention have been described, other embodiments may exist. While the specification includes a detailed description, the invention's scope is indicated by the following claims. Furthermore, while the specification has been described in language specific to structural features and/or methodological acts, the claims are not limited to the features or acts described above. Rather, the specific features and acts described above are disclosed as illustrative aspects and embodiments of the invention. Various other aspects, embodiments, modifications, and equivalents thereof which, after reading the description herein, may suggest themselves to one of ordinary skill in the art without departing from the spirit of the present invention or the scope of the claimed subject matter.

What is claimed is:

1. A method of detecting proteasome activity in a target cell comprising:
    a) contacting a biological sample comprising whole blood comprising peripheral blood mononuclear cells with an IκB (inhibitor of kappa B) degradation agonist to activate the peripheral blood mononuclear cells in the biological sample, wherein
    the IκB degradation agonist is selected from the group consisting of lipopolysaccharide (LPS), CD40L, PMA, IL-1, IL-4, G-CSF, SCF, Flt-3 ligand, GM-CSF, TGF, anti-CD28, anti-CD3/CD28, TNF-alpha, glucuronoxylomannan from *Cryptococcus*, and monophosphoryl lipid A;
    b) contacting the activated biological sample with a first labeled binding agent that is an antibody capable of binding IκB;
    c) detecting a target cell in the biological sample of b); and
    d) determining an amount of the first labeled binding agent bound to the detected target cell, thereby detecting proteasome activity in the target cell.

2. The method of claim 1, wherein detecting the target cell in the biological sample comprises contacting the biological sample with a second labeled binding agent that is an antibody capable of binding the target cell.

3. The method of claim 2, further comprising contacting the activated biological sample with a third labeled binding agent that is an antibody capable of binding an activatable protein and detecting an amount of the third labeled binding agent bound to the detected target cell.

4. The method of claim 3, wherein the activatable protein is P-ERK, P-Akt, P-p38, P-SAPK, or P-S6.

5. The method of claim 3, wherein each of the first, second, and third labeled binding agents is independently labeled with a detectable moiety.

6. The method of claim 3, comprising detecting the amount of first, second, and/or third labeled binding agent bound to the detected target cell, wherein the target cell is a hematopoietic cell, wherein the hematopoietic cell is bound to:
    the first, second, or third labeled binding agent;
    the first and second labeled binding agents;
    the first and third labeled binding agents;
    the second and third labeled binding agents; or
    the first, second, and third labeled binding agents.

7. The method of claim 6, further comprising comparing the amount of first, second, and/or third labeled binding agents bound to the detected hematopoietic cell to an amount of first, second, and/or third labeled binding agents bound to a hematopoietic cell in a control sample.

8. The method of claim 7, wherein the control sample is a biological sample that has not been contacted with a proteasome effector and/or the IκB degradation agonist.

9. The method of claim 2, wherein the second labeled binding agent is an antibody capable of binding a cellular surface antigen of the target cell.

10. The method of claim 9, wherein the second labeled binding agent is an antibody specific for a cellular surface antigen selected from the group consisting of CD3, CD4, CD8, CD10, CD11a, CD14, CD15, CD16, CD19, CD20, CD24, CD25, CD30, CD31, CD34, CD38, CD45, CD53, CD56, CD61, CD91, CD114, CD117, CD138, and CD182.

11. The method of claim 1, wherein the first labeled binding agent is an antibody that specifically binds IκBalpha, IκBbeta, IκBepsilon, IκBgamma, BCL-3, p100, or p105.

12. The method of claim 1, wherein the IκB degradation agonist is a toll-like receptor 4 (TLR4) agonist.

13. The method of claim 1, wherein the IκB degradation agonist is LPS, CD40L, PMA, TGF, or TNF-alpha.

14. The method of claim 1, further comprising contacting the activated biological sample with a fixative agent.

15. The method of claim 14, further comprising contacting the one or more target cells in the fixed biological sample with a permeabilizing agent before contacting the biological sample with the first labeled binding agent.

16. The method of claim 1, wherein the peripheral blood mononuclear cells comprise monocytes.

17. A method of determining an effect of a proteasome activity on a target cell comprising:
a) contacting a biological sample comprising whole blood comprising peripheral blood mononuclear cells with a proteasome effector;
b) contacting the biological sample treated with the proteasome effector with an IκB degradation agonist to activate the peripheral blood mononuclear cells in the biological sample, wherein
the IκB degradation agonist is selected from the group consisting of lipopolysaccharide (LPS), CD40L, PMA, IL-1, IL-4, G-CSF, SCF, Flt-3 ligand, GM-CSF, TGF, anti-CD28, anti-CD3/CD28, TNF-alpha, glucuronoxylomannan from *Cryptococcus*, and monophosphoryl lipid A;
c) contacting the activated biological sample with a first labeled binding agent that is an antibody capable of binding IκB;
d) detecting a target cell in the biological sample of c);
e) determining an amount of the first labeled binding agent bound to the detected target cell, thereby detecting an amount of proteasome activity in the target cell in the presence of the proteasome effector; and
f) comparing the amount of proteasome activity of the target cell in the presence of the proteasome effector to a target cell in the absence of the proteasome effector, thereby determining an effect of the proteasome effector on the proteasome activity in the target cell.

18. The method of claim 17, wherein the proteasome effector is a proteasome inhibitor.

19. The method of claim 18, wherein the proteasome inhibitor is a non-covalent proteasome inhibitor, a reversible covalent proteasome inhibitor, or an irreversible covalent proteasome inhibitor.

20. The method of claim 17, wherein the peripheral blood mononuclear cells comprise monocytes.

21. A method of identifying a proteasome effector comprising:
a) contacting a biological sample comprising whole blood comprising peripheral blood mononuclear cells with a candidate proteasome effector, wherein
the IκB degradation agonist is selected from the group consisting of lipopolysaccharide (LPS), CD40L, PMA, IL-1, IL-4, G-CSF, SCF, Flt-3 ligand, GM-CSF, TGF, anti-CD28, anti-CD3/CD28, TNF-alpha, glucuronoxylomannan from *Cryptococcus*, and monophosphoryl lipid A;
b) contacting the biological sample treated with the candidate proteasome effector with an IκB degradation agonist to activate the peripheral blood mononuclear cells in the biological sample;
c) contacting the activated biological sample with a first labeled binding agent that is an antibody capable of binding IκB;
d) detecting a target cell in the biological sample of c);
e) detecting an amount of the first labeled binding agent bound to the detected target cell; and
f) comparing the amount of the first labeled binding agent bound to the detected target cell to a control sample, wherein a difference in the amount of the first labeled binding agent bound to the detected target cell compared to the control sample indicates the candidate is a proteasome effector.

22. The method of claim 21, wherein the peripheral blood mononuclear cells comprise monocytes.

* * * * *